(12) United States Patent
Freeman et al.

(10) Patent No.: US 8,439,872 B2
(45) Date of Patent: May 14, 2013

(54) APPARATUS AND METHOD FOR PENETRATION WITH SHAFT HAVING A SENSOR FOR SENSING PENETRATION DEPTH

(75) Inventors: Dominique Freeman, La Honda, CA (US); Thomas Schulte, Redmond, WA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/767,311

(22) Filed: Apr. 26, 2010

(65) Prior Publication Data

US 2010/0228194 A1  Sep. 9, 2010

Related U.S. Application Data

(63) Continuation of application No. 10/008,159, filed on Nov. 6, 2001, now Pat. No. 7,780,631, which is a continuation of application No. 09/050,853, filed on Mar. 30, 1998, now Pat. No. 6,391,005.

(51) Int. Cl.
*A61M 5/00* (2006.01)

(52) U.S. Cl.
USPC .......................................................... 604/117

(58) Field of Classification Search .......... 604/117, 604/192, 93.01, 264; 600/573, 583
See application file for complete search history.

(56) References Cited

U.S. PATENT DOCUMENTS

| | | | | |
|---|---|---|---|---|
| 2,061 A | 4/1841 | Osdel | | 606/182 |
| 55,620 A | 6/1866 | Capewell | | 606/181 |
| 657,646 A | 9/1900 | Haviland | | 435/4 |
| 1,135,465 A | 4/1915 | Pollock | | 606/181 |
| 1,733,847 A | 10/1929 | Wilmot | | 292/332 |
| 2,258,857 A | 10/1941 | McCann | | 601/81 |
| 2,628,319 A | 2/1953 | Vang | | 310/15 |
| 2,714,890 A | 8/1955 | Alfred | | 606/169 |
| 2,763,935 A | 9/1956 | Whaley | | 33/511 |
| 2,801,633 A | 8/1957 | Ehrlich | | 606/181 |

(Continued)

FOREIGN PATENT DOCUMENTS

| | | |
|---|---|---|
| DE | 2206674 | 8/1972 |
| DE | 3538313 A1 | 4/1986 |

(Continued)

OTHER PUBLICATIONS

Wolfbeis et al. (Sol-gel based glucose biosensors employing optical oxygen transducers, and a method for compensating for variable oxygen background, Biosensors & Bioelectronics 15 (2000) pp. 69-76).

*Primary Examiner* — Christopher D Koharski
(74) *Attorney, Agent, or Firm* — Paul Davis; Goodwin Procter LLP

(57) ABSTRACT

An apparatus having a shaft that can sense the depth of penetration, for penetrating into an object (the substrate). The substrate being penetrated has impedance that varies according to the depth under a surface of the substrate. The shaft has a tip for penetration and has conductive ends near to the tip of the shaft. A change of impedance of material of the object between the conductive ends can be sensed to provide information on the depth of penetration. A processor can be provided external to the object being penetrated by the shaft to gather and process the impedance information to determine whether the desired depth has been achieved.

17 Claims, 5 Drawing Sheets

U.S. PATENT DOCUMENTS

| | | | | |
|---|---|---|---|---|
| 2,880,876 A | 4/1959 | Dujardin | | 210/523 |
| 3,046,987 A | 7/1962 | Ehrlich | | 128/314 |
| 3,030,959 A | 9/1962 | Grunert | | 128/329 |
| 3,086,288 A | 4/1963 | Balamuth | | 30/277.4 |
| 3,090,384 A | 5/1963 | Baldwin et al. | | 604/272 |
| 3,208,452 A | 9/1965 | Stern | | 606/182 |
| 3,358,689 A | 12/1967 | Higgins | | 128/329 |
| 3,412,729 A | 11/1968 | Smith, Jr. | | 128/2.05 |
| 3,448,307 A | 6/1969 | Rudolph | | 310/23 |
| 3,494,358 A | 2/1970 | Grossenbacher | | 128/218 |
| 3,620,209 A | 11/1971 | Kravitz | | 601/79 |
| 3,626,929 A | 12/1971 | Sanz | | 128/2 R |
| 3,628,026 A | 12/1971 | Cronin | | 250/214.1 |
| 3,665,672 A | 5/1972 | Speelman | | 53/435 |
| 3,673,475 A | 6/1972 | Britton | | 318/122 |
| 3,712,293 A | 1/1973 | Mielke, Jr. | | 128/2 G |
| 3,734,812 A | 5/1973 | Yazawa | | 428/107 |
| 3,742,954 A | 7/1973 | Strickland | | 128/302 |
| 3,780,960 A | 12/1973 | Tokuno | | 242/555.2 |
| 3,832,776 A | 9/1974 | Sawyer | | 30/272 |
| 3,836,148 A | 9/1974 | Manning | | 273/368 |
| 3,851,543 A | 12/1974 | Krom | | 74/493 |
| 3,853,010 A | 12/1974 | Christen | | 73/864.24 |
| 3,924,818 A | 12/1975 | Pfeifle | | 242/364.7 |
| 3,938,526 A | 2/1976 | Anderson | | 128/303.1 |
| 3,953,172 A | 4/1976 | Shapiro | | 23/230 |
| 3,971,365 A | 7/1976 | Smith | | 128/2.17 |
| 4,057,394 A | 11/1977 | Genshaw | | 23/230 |
| 4,077,406 A | 3/1978 | Sandhage | | 604/61 |
| 4,109,655 A | 8/1978 | Chaconac | | 128/253 |
| 4,139,011 A | 2/1979 | Benoit | | 606/182 |
| 4,154,228 A | 5/1979 | Feldstein | | 606/169 |
| 4,168,130 A | 9/1979 | Barth | | 404/99 |
| 4,184,486 A | 1/1980 | Papa | | 600/373 |
| 4,190,420 A | 2/1980 | Covington | | 422/63 |
| 4,191,193 A | 3/1980 | Seo | | 600/488 |
| 4,193,690 A | 3/1980 | Levenson | | 356/301 |
| 4,203,446 A | 5/1980 | Hofert | | 606/182 |
| 4,207,870 A | 6/1980 | Eldridge | | 128/766 |
| 4,223,674 A | 9/1980 | Fluent | | 604/504 |
| 4,224,125 A | 9/1980 | Nakamura | | 204/195 B |
| 4,224,949 A | 9/1980 | Scott | | 128/734 |
| 4,230,118 A | 10/1980 | Holman et al. | | 128/314 |
| 4,240,439 A | 12/1980 | Abe | | 600/412 |
| 4,254,083 A | 3/1981 | Columbus | | 422/55 |
| 4,258,001 A | 3/1981 | Pierce | | 422/56 |
| 4,259,653 A | 3/1981 | McGonigal | | 310/15 |
| 4,299,230 A * | 11/1981 | Kubota | | 600/300 |
| 4,301,412 A | 11/1981 | Hill | | 324/442 |
| 4,321,397 A | 3/1982 | Nix | | 548/366 |
| 4,338,174 A | 7/1982 | Tamura | | 204/195 |
| 4,340,669 A | 7/1982 | Bauer | | 435/14 |
| 4,350,762 A | 9/1982 | De Luca | | 435/10 |
| 4,353,984 A | 10/1982 | Yamada | | 435/14 |
| 4,356,826 A | 11/1982 | Kubota | | 600/300 |
| 4,360,016 A | 11/1982 | Sarrine | | 128/763 |
| 4,388,922 A | 6/1983 | Telang | | 604/319 |
| 4,391,905 A | 7/1983 | Bauer | | 435/14 |
| 4,391,906 A | 7/1983 | Bauer | | 435/14 |
| 4,392,933 A | 7/1983 | Nakamura | | 204/403.14 |
| 4,394,512 A | 7/1983 | Batz | | 548/365 |
| 4,397,556 A | 8/1983 | Muller | | 356/301 |
| 4,407,008 A | 9/1983 | Schmidt | | 356/301 |
| 4,411,266 A | 10/1983 | Cosman | | 128/303.18 |
| 4,414,975 A | 11/1983 | Ryder | | 128/314 |
| 4,418,037 A | 11/1983 | Katsuyama et al. | | 422/56 |
| 4,420,564 A | 12/1983 | Tsuji | | 435/288 |
| 4,425,039 A | 1/1984 | Grant | | 356/35.5 |
| 4,426,451 A | 1/1984 | Columbus | | 436/518 |
| 4,426,884 A | 1/1984 | Polchaninoff | | 73/172 |
| 4,440,301 A | 4/1984 | Intengan | | 206/456 |
| 4,442,814 A | 4/1984 | Meinecke | | 128/314 |
| 4,442,972 A | 4/1984 | Sahay | | 236/1 EA |
| 4,449,529 A | 5/1984 | Burns | | 606/182 |
| 4,462,405 A | 7/1984 | Ehrlich | | 606/182 |
| 4,469,110 A | 9/1984 | Slama | | 128/770 |
| 4,517,978 A | 5/1985 | Levin | | 128/314 |
| 4,518,384 A | 5/1985 | Tarello | | 604/61 |
| 4,523,994 A | 6/1985 | Shono | | 549/352 |
| 4,535,769 A | 8/1985 | Burns | | 128/314 |
| 4,535,773 A | 8/1985 | Yoon | | 606/185 |
| 4,537,197 A | 8/1985 | Hulka | | 128/633 |
| 4,539,988 A | 9/1985 | Shirley | | 128/314 |
| 4,545,382 A | 10/1985 | Higgins | | 128/635 |
| 4,553,541 A | 11/1985 | Burns | | 128/314 |
| 4,561,445 A | 12/1985 | Berke | | 128/642 |
| 4,577,630 A | 3/1986 | Nitzsche | | 128/314 |
| 4,580,564 A | 4/1986 | Anderson | | 502/8 |
| 4,580,565 A | 4/1986 | Cornell | | 128/314 |
| 4,586,819 A | 5/1986 | Tochigi | | 356/301 |
| 4,586,926 A | 5/1986 | Osborne | | 604/272 |
| 4,590,411 A | 5/1986 | Kelly | | 318/687 |
| 4,595,479 A | 6/1986 | Kimura | | 204/294 |
| 4,600,014 A | 7/1986 | Beraha | | 128/754 |
| 4,603,209 A | 7/1986 | Tsien | | 549/352 |
| 4,608,997 A | 9/1986 | Conway | | 128/763 |
| 4,615,340 A | 10/1986 | Cronenberg | | 128/635 |
| 4,616,649 A | 10/1986 | Burns | | 128/314 |
| 4,619,754 A | 10/1986 | Niki | | 204/290 |
| 4,622,974 A | 11/1986 | Coleman | | 128/634 |
| 4,624,253 A | 11/1986 | Burns | | 128/314 |
| 4,627,445 A | 12/1986 | Garcia | | 600/583 |
| 4,637,393 A | 1/1987 | Ray | | 128/305 |
| 4,637,403 A | 1/1987 | Garcia | | 600/583 |
| 4,643,189 A | 2/1987 | Mintz | | 128/314 |
| 4,648,408 A | 3/1987 | Hutcheson | | 128/770 |
| 4,648,714 A | 3/1987 | Benner | | 356/301 |
| 4,653,511 A | 3/1987 | Goch | | 128/763 |
| 4,653,513 A | 3/1987 | Dombrowski | | 600/578 |
| 4,655,225 A | 4/1987 | Dahne | | 600/316 |
| 4,661,768 A | 4/1987 | Carusillo | | 324/678 |
| 4,666,438 A | 5/1987 | Raulerson | | 604/272 |
| 4,676,244 A | 6/1987 | Enstrom | | 128/314 |
| 4,677,979 A | 7/1987 | Burns | | 128/314 |
| 4,678,277 A | 7/1987 | Delhaye | | 356/301 |
| 4,682,892 A | 7/1987 | Chawla | | 356/353 |
| 4,702,594 A | 10/1987 | Grant | | 356/35.5 |
| 4,711,245 A | 12/1987 | Higgins | | 128/635 |
| 4,712,460 A | 12/1987 | Allen | | 83/208 |
| 4,712,548 A | 12/1987 | Enstrom | | 128/314 |
| 4,714,462 A | 12/1987 | DiDomenico | | 604/67 |
| 4,715,374 A | 12/1987 | Maggio | | 128/314 |
| 4,731,330 A | 3/1988 | Hilll | | 436/16 |
| 4,731,726 A | 3/1988 | Allen, III | | 600/300 |
| 4,734,360 A | 3/1988 | Phillips | | 435/25 |
| 4,735,203 A | 4/1988 | Ryder | | 128/314 |
| 4,737,458 A | 4/1988 | Batz | | 435/28 |
| 4,750,489 A | 6/1988 | Berkman | | 606/166 |
| 4,753,776 A | 6/1988 | Hillman | | 422/101 |
| 4,756,884 A | 7/1988 | Hillman | | 422/73 |
| 4,757,022 A | 7/1988 | Shults | | 204/403.05 |
| 4,758,323 A | 7/1988 | Davis | | 204/403 |
| 4,774,192 A | 9/1988 | Teriniello | | 436/530 |
| 4,784,486 A | 11/1988 | Van Wagenen | | 356/301 |
| 4,787,398 A | 11/1988 | Garcia | | 600/583 |
| 4,790,979 A | 12/1988 | Teriniello | | 422/56 |
| 4,794,926 A | 1/1989 | Munsch et al. | | 606/183 |
| 4,797,283 A | 1/1989 | Allen | | 424/443 |
| 4,814,142 A | 3/1989 | Gleisner | | 422/56 |
| 4,814,661 A | 3/1989 | Ratzlaff | | 310/328 |
| 4,817,603 A | 4/1989 | Turner | | 606/182 |
| 4,818,493 A | 4/1989 | Coville | | 422/102 |
| 4,820,010 A | 4/1989 | Sciefres | | 385/43 |
| 4,820,399 A | 4/1989 | Senda | | 204/403 |
| 4,823,806 A | 4/1989 | Bajada | | 600/557 |
| 4,824,639 A | 4/1989 | Hildenbrand | | 422/56 |
| RE32,922 E | 5/1989 | Levin | | 128/314 |
| 4,825,711 A | 5/1989 | Jensen | | 73/865.8 |
| 4,827,763 A | 5/1989 | Bourland | | 73/172 |
| 4,829,011 A | 5/1989 | Gibbons | | 436/512 |
| 4,830,959 A | 5/1989 | McNeill | | 435/53 |
| 4,836,904 A | 6/1989 | Armstron | | 204/294 |
| 4,840,893 A | 6/1989 | Hill | | 435/6 |
| 4,844,095 A | 7/1989 | Chiodo | | 128/314 |
| 4,845,392 A | 7/1989 | Mumbower | | 310/14 |
| 4,850,973 A | 7/1989 | Jordan | | 604/157 |
| 4,857,274 A | 8/1989 | Simon | | 422/72 |

| Patent | Date | Inventor | Class |
|---|---|---|---|
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |
| 4,900,424 A | 2/1990 | Birch | 204/409 |
| 4,900,666 A | 2/1990 | Phillips | 435/25 |
| 4,911,794 A | 3/1990 | Parce | 204/1 T |
| 4,920,977 A | 5/1990 | Haynes | 128/770 |
| 4,924,879 A | 5/1990 | O'brien | 600/583 |
| 4,935,346 A | 6/1990 | Phillips | 435/14 |
| 4,938,218 A | 7/1990 | Goodman | 128/633 |
| 4,940,468 A | 7/1990 | Petillo | 606/170 |
| 4,944,304 A | 7/1990 | Nishina | 128/667 |
| 4,945,045 A | 7/1990 | Forrest | 435/25 |
| 4,946,795 A | 8/1990 | Gibbons | 436/179 |
| 4,948,727 A | 8/1990 | Cass | 435/18 |
| 4,948,961 A | 8/1990 | Hillman | 250/252.1 |
| 4,952,373 A | 8/1990 | Sugarman | 422/99 |
| 4,952,515 A | 8/1990 | Gleisner | 436/169 |
| 4,953,552 A | 9/1990 | DeMarzo | 128/635 |
| 4,953,976 A | 9/1990 | Adler-Golden | 356/301 |
| 4,963,498 A | 10/1990 | Hillman | 436/69 |
| 4,966,581 A | 10/1990 | Landau | 604/72 |
| 4,966,646 A | 10/1990 | Zdeblick | 156/633 |
| 4,966,671 A | 10/1990 | Nylander | 204/153.14 |
| 4,975,581 A | 12/1990 | Robinson | 250/339 |
| 4,976,724 A | 12/1990 | Nieto | 606/182 |
| 4,977,910 A | 12/1990 | Miyahara | 134/7 |
| 4,983,178 A | 1/1991 | Schnell | 606/181 |
| 4,984,085 A | 1/1991 | Landowski | 358/213 |
| 4,990,154 A | 2/1991 | Brown | 606/182 |
| 4,995,402 A | 2/1991 | Smith | 600/584 |
| 4,999,582 A | 3/1991 | Parks | 324/438 |
| 5,001,054 A | 3/1991 | Wagner | 435/14 |
| 5,001,873 A | 3/1991 | Rufin | 451/39 |
| 5,004,923 A | 4/1991 | Hillman | 250/341 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| D318,331 S | 7/1991 | Phillips | D24/169 |
| 5,028,142 A | 7/1991 | Ostoich et al. | 366/273 |
| 5,029,583 A | 7/1991 | Meserol | 600/316 |
| 5,035,704 A | 7/1991 | Lambert | 606/182 |
| 5,039,617 A | 8/1991 | McDonald | 436/69 |
| 5,043,143 A | 8/1991 | Shaw | 422/65 |
| 5,046,496 A | 9/1991 | Betts | 600/352 |
| 5,047,044 A | 9/1991 | Smith | 606/182 |
| 5,049,373 A | 9/1991 | Tsien | 549/352 |
| 5,049,487 A | 9/1991 | Phillips | 435/4 |
| 5,054,487 A | 10/1991 | Clarke | 128/633 |
| 5,054,499 A | 10/1991 | Swierczek | 128/770 |
| 5,057,082 A | 10/1991 | Burchette, Jr. | 604/164 |
| 5,057,277 A | 10/1991 | Mauze | 422/56 |
| 5,059,394 A | 10/1991 | Phillips | 422/68.1 |
| 5,059,789 A | 10/1991 | Salcudean | 250/206.1 |
| 5,060,174 A | 10/1991 | Gross | 702/139 |
| 5,062,898 A | 11/1991 | McDermott | 134/7 |
| 5,064,411 A | 11/1991 | Gordon, III | 604/48 |
| 5,070,874 A | 12/1991 | Barnes | 128/633 |
| 5,070,886 A | 12/1991 | Mitchen | 128/771 |
| 5,074,872 A | 12/1991 | Brown | 606/182 |
| 5,077,017 A | 12/1991 | Gorin | 422/100 |
| 5,077,199 A | 12/1991 | Basagni | 435/14 |
| 5,080,865 A | 1/1992 | Leiner | 422/68.1 |
| 5,086,229 A | 2/1992 | Rosenthal | 250/341 |
| 5,089,112 A | 2/1992 | Skotheim | 204/403 |
| 5,092,842 A | 3/1992 | Bechtold | 604/135 |
| 5,094,943 A | 3/1992 | Siedel | 435/25 |
| 5,096,669 A | 3/1992 | Lauks | 204/403.02 |
| 5,097,810 A | 3/1992 | Fishman | 600/556 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,104,813 A | 4/1992 | Besemer | 436/179 |
| 5,107,764 A | 4/1992 | Gasparrini | 101/425 |
| 5,108,564 A | 4/1992 | Szuminsky | 204/153.12 |
| 5,108,889 A | 4/1992 | Smith | 435/4 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,132,801 A | 7/1992 | Yamano | 358/213 |
| 5,133,730 A | 7/1992 | Biro | 606/182 |
| 5,135,719 A | 8/1992 | Hillman | 422/101 |
| 5,139,685 A | 8/1992 | Castro | 210/767 |
| 5,140,161 A | 8/1992 | Hillman | 250/341 |
| 5,141,868 A | 8/1992 | Shanks | 435/288 |
| 5,144,139 A | 9/1992 | Hillman | 250/341 |
| 5,145,565 A | 9/1992 | Kater | 600/341 |
| 5,146,091 A | 9/1992 | Knudson | 250/341.6 |
| 5,152,296 A | 10/1992 | Simons | 128/670 |
| 5,152,775 A | 10/1992 | Ruppert | 606/182 |
| 5,153,671 A | 10/1992 | Miles | 356/301 |
| 5,156,611 A | 10/1992 | Haynes | 606/181 |
| 5,162,525 A | 11/1992 | Masilamani | 549/352 |
| 5,163,442 A | 11/1992 | Ono | 128/760 |
| 5,164,598 A | 11/1992 | Hillman | 250/341 |
| 5,167,619 A | 12/1992 | Wuchinich | 604/22 |
| 5,170,364 A | 12/1992 | Gross | 702/139 |
| 5,174,726 A | 12/1992 | Findlay | 417/205 |
| D332,490 S | 1/1993 | Brown | D24/146 |
| 5,178,142 A | 1/1993 | Harjunmaa | 128/633 |
| 5,179,005 A | 1/1993 | Phillips | 435/14 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 600/566 |
| 5,189,751 A | 3/1993 | Giuliani | 15/22.1 |
| 5,192,415 A | 3/1993 | Yoshioka | 204/403 |
| 5,194,391 A | 3/1993 | Mauze | 436/166 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,209,028 A | 5/1993 | McDermott | 51/426 |
| 5,211,652 A | 5/1993 | Derbyshire | 606/182 |
| 5,212,879 A | 5/1993 | Biro | 29/437 |
| 5,215,587 A | 6/1993 | McConnellogue | 118/699 |
| 5,216,597 A | 6/1993 | Beckers | 364/413.02 |
| 5,217,476 A | 6/1993 | Wishinsky | 606/167 |
| 5,217,480 A | 6/1993 | Haber | 606/182 |
| 5,218,966 A | 6/1993 | Yamasawa | 600/499 |
| 5,222,504 A | 6/1993 | Solomon | 600/557 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,241,969 A | 9/1993 | Carson | 600/566 |
| 5,247,932 A | 9/1993 | Chung | 128/633 |
| 5,249,583 A | 10/1993 | Mallaby | 600/567 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| 5,266,359 A | 11/1993 | Spielvogel | 427/388.4 |
| D342,573 S | 12/1993 | Cerola | D24/147 |
| 5,267,974 A | 12/1993 | Lambert | 604/195 |
| 5,272,087 A | 12/1993 | El Murr | 435/291 |

| Patent No. | Kind | Date | Name | Class |
|---|---|---|---|---|
| 5,277,181 | A | 1/1994 | Mendelson | 128/633 |
| 5,279,294 | A | 1/1994 | Anderson | 600/322 |
| 5,279,791 | A | 1/1994 | Aldrich | 422/58 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollman | 435/288 |
| 5,294,261 | A | 3/1994 | McDermott | 134/7 |
| 5,296,378 | A | 3/1994 | Sakata | 436/63 |
| 5,300,779 | A | 4/1994 | Hillman | 250/341 |
| 5,304,192 | A | 4/1994 | Crouse | 606/181 |
| 5,304,193 | A | 4/1994 | Zhadanov | 606/182 |
| 5,304,347 | A | 4/1994 | Mann | 422/67 |
| 5,304,468 | A | 4/1994 | Phillips | 435/14 |
| 5,306,623 | A | 4/1994 | Kiser | 435/14 |
| 5,307,263 | A | 4/1994 | Brown | 600/301 |
| 5,312,590 | A | 5/1994 | Gunasingham | 422/56 |
| 5,314,441 | A | 5/1994 | Cusack | 606/182 |
| 5,314,442 | A | 5/1994 | Morita | 606/182 |
| 5,315,793 | A | 5/1994 | Peterson | 451/2 |
| 5,316,012 | A | 5/1994 | Siegal | 128/744 |
| 5,318,583 | A | 6/1994 | Rabenau | 606/182 |
| 5,318,584 | A | 6/1994 | Lange | 606/182 |
| 5,320,607 | A | 6/1994 | Ishibashi | 604/115 |
| 5,320,808 | A | 6/1994 | Holen | 422/64 |
| 5,324,302 | A | 6/1994 | Crouse | 606/181 |
| 5,324,303 | A | 6/1994 | Strong | 606/181 |
| 5,330,634 | A | 7/1994 | Wong | 205/777.5 |
| 5,332,479 | A | 7/1994 | Uenoyama | 204/153.12 |
| 5,341,206 | A | 8/1994 | Pittaro | 356/301 |
| 5,342,382 | A | 8/1994 | Brinkerhoff | 606/184 |
| 5,344,703 | A | 9/1994 | Kovar | 428/312.6 |
| 5,350,392 | A | 9/1994 | Purcell | 606/182 |
| 5,352,351 | A | 10/1994 | White | 204/406 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,365,699 | A | 11/1994 | Armstrong | 451/7 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,368,047 | A | 11/1994 | Suzuki | 600/578 |
| 5,370,509 | A | 12/1994 | Golding | 417/423.1 |
| 5,371,687 | A | 12/1994 | Holmes | 364/514 |
| 5,372,135 | A | 12/1994 | Mendelson | 600/322 |
| 5,375,397 | A | 12/1994 | Ferrand | 54/66 |
| 5,378,628 | A | 1/1995 | Graetzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentezkow | 435/180 |
| 5,390,450 | A | 2/1995 | Goenka | 451/39 |
| 5,393,903 | A | 2/1995 | Graetzel | 556/137 |
| 5,395,339 | A | 3/1995 | Talonn | 604/111 |
| 5,395,387 | A | 3/1995 | Burns | 606/181 |
| 5,397,334 | A | 3/1995 | Schenk | 606/182 |
| 5,401,376 | A | 3/1995 | Foos | 204/415 |
| 5,402,798 | A | 4/1995 | Swierczek | 128/770 |
| 5,405,283 | A | 4/1995 | Goenka | 451/39 |
| 5,405,510 | A | 4/1995 | Betts | 205/782 |
| 5,405,511 | A | 4/1995 | White | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | Gentezkow | 435/180 |
| 5,409,583 | A | 4/1995 | Yoshioka | 204/153.12 |
| 5,409,664 | A | 4/1995 | Allen | 422/56 |
| 5,410,059 | A | 4/1995 | Fraser | 546/10 |
| 5,415,169 | A | 5/1995 | Siczek | 600/427 |
| 5,418,142 | A | 5/1995 | Kiser | 435/14 |
| 5,423,847 | A | 6/1995 | Strong et al. | 606/182 |
| 5,424,545 | A | 6/1995 | Block | 350/343 |
| 5,426,032 | A | 6/1995 | Phillips | 435/14 |
| 5,436,161 | A | 7/1995 | Bergstrom | 435/291 |
| 5,437,999 | A | 8/1995 | Diebold | 435/288 |
| 5,438,271 | A | 8/1995 | White | 324/444 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,453,360 | A | 9/1995 | Yu | 435/28 |
| 5,454,828 | A | 10/1995 | Schraga | 606/181 |
| 5,456,875 | A | 10/1995 | Lambert | 264/328.1 |
| 5,459,325 | A | 10/1995 | Hueton | 250/458.1 |
| 5,460,182 | A | 10/1995 | Goodman | 600/342 |
| 5,462,533 | A | 10/1995 | Daugherty | 604/164 |
| 5,464,418 | A | 11/1995 | Schraga | 606/182 |
| 5,465,722 | A | 11/1995 | Fort | 600/447 |
| 5,471,102 | A | 11/1995 | Becker | 310/50 |
| 5,472,427 | A | 12/1995 | Rammler | 604/164.01 |
| 5,474,084 | A | 12/1995 | Cunniff | 600/557 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| D367,109 | S | 2/1996 | Ryner | D24/224 |
| 5,490,505 | A | 2/1996 | Diab | 600/323 |
| 5,496,274 | A | 3/1996 | Graves | 604/86 |
| 5,496,453 | A | 3/1996 | Uenoyama | 205/777.5 |
| 5,498,542 | A | 3/1996 | Corey | 435/283.1 |
| 5,501,836 | A | 3/1996 | Myerson | 42/57 |
| 5,501,893 | A | 3/1996 | Laermer | 428/161 |
| 5,507,288 | A | 4/1996 | Bocker | 128/633 |
| 5,507,629 | A | 4/1996 | Jarvik | 417/423.3 |
| 5,508,171 | A | 4/1996 | Walling | 205/777.5 |
| 5,509,410 | A | 4/1996 | Hill | 128/637 |
| 5,510,266 | A | 4/1996 | Bonner et al. | 436/43 |
| 5,512,159 | A | 4/1996 | Yoshioka | 204/403 |
| 5,514,152 | A | 5/1996 | Smith | 606/182 |
| 5,515,170 | A | 5/1996 | Matzinger | 356/423 |
| 5,518,006 | A | 5/1996 | Mawhirt | 128/770 |
| D371,198 | S | 6/1996 | Savage | D24/142 |
| 5,524,636 | A | 6/1996 | Sarvazyan | 128/774 |
| 5,525,511 | A | 6/1996 | D'Costa | 435/287.9 |
| 5,525,518 | A | 6/1996 | Lundsgaard | 436/68 |
| 5,526,120 | A | 6/1996 | Jina | 356/446 |
| 5,527,333 | A | 6/1996 | Nikkels | 606/182 |
| 5,527,334 | A | 6/1996 | Kanner | 606/182 |
| 5,529,074 | A | 6/1996 | Greenfield | 600/557 |
| 5,540,676 | A | 7/1996 | Freiberg | 606/3 |
| 5,540,709 | A | 7/1996 | Ramel | 606/183 |
| 5,543,326 | A | 8/1996 | Heller | 435/287.9 |
| 5,545,174 | A | 8/1996 | Schenk | 606/182 |
| 5,545,291 | A | 8/1996 | Smith | 438/107 |
| 5,547,702 | A | 8/1996 | Gleisner | 427/2.13 |
| D373,419 | S | 9/1996 | Muramatsu | D24/165 |
| 5,554,153 | A | 9/1996 | Costello | 606/9 |
| 5,554,166 | A | 9/1996 | Lange | 606/182 |
| 5,558,834 | A | 9/1996 | Chu | 422/55 |
| 5,562,384 | A | 10/1996 | Alvite | 414/226.01 |
| 5,562,696 | A | 10/1996 | Nobles | 606/185 |
| 5,563,031 | A | 10/1996 | Yu | 435/4 |
| 5,563,042 | A | 10/1996 | Phillips | 435/14 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,284 | A | 11/1996 | Athan | 600/323 |
| 5,575,403 | A | 11/1996 | Charlton | 221/31 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,591,139 | A | 1/1997 | Lin | 604/264 |
| 5,593,852 | A | 1/1997 | Heller | 435/14 |
| 5,599,501 | A | 2/1997 | Carey | 422/64 |
| 5,605,837 | A | 2/1997 | Karimi | 436/14 |
| D378,612 | S | 3/1997 | Clark | D24/169 |
| 5,608,006 | A | 3/1997 | Myerson | 525/54.1 |
| 5,609,749 | A | 3/1997 | Yamauchi | 205/777.5 |
| 5,611,809 | A | 3/1997 | Marshall | 606/181 |
| 5,611,810 | A | 3/1997 | Arnold | 606/185 |
| 5,613,978 | A | 3/1997 | Harding | 606/181 |
| 5,616,135 | A | 4/1997 | Thorne | 604/192 |
| 5,617,851 | A | 4/1997 | Lipkovker | 600/573 |
| 5,618,297 | A | 4/1997 | Hart | 606/185 |
| 5,620,279 | A | 4/1997 | Furusawa et al. | 204/402 |
| 5,620,863 | A | 4/1997 | Tomasco | 435/14 |
| 5,624,458 | A | 4/1997 | Lipscher | 606/181 |
| 5,624,459 | A | 4/1997 | Kortenbach | 606/185 |
| 5,624,537 | A | 4/1997 | Turner | 204/403 |
| D379,516 | S | 5/1997 | Rutter | D24/146 |
| 5,628,764 | A | 5/1997 | Schraga | 606/182 |

| Patent No. | Date | Inventor | Class |
|---|---|---|---|
| 5,628,765 A | 5/1997 | Morita | 606/182 |
| 5,628,890 A | 5/1997 | Carter | 204/403 |
| 5,628,961 A | 5/1997 | Davis | 422/63 |
| 5,630,828 A | 5/1997 | Mawhirt | 606/187 |
| 5,630,986 A | 5/1997 | Charlton | 422/64 |
| 5,632,410 A | 5/1997 | Moulton | 221/79 |
| 5,640,954 A | 6/1997 | Pfeiffer | 128/635 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Hansen et al. | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/573 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Morita | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A * | 4/1998 | Lee | 606/189 |
| 5,736,103 A | 4/1998 | Pugh | 422/68.1 |
| 5,738,244 A | 4/1998 | Charlton | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Morita | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons | 210/643 |
| 5,770,369 A | 6/1998 | Meade | 435/6 |
| 5,772,586 A | 6/1998 | Heinonen | 600/309 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian et al. | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| D403,975 S | 1/1999 | Douglas | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon et al. | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons | 606/181 |
| 5,872,713 A | 2/1999 | Douglas | 702/85 |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roper | 606/344 |
| 5,880,829 A | 3/1999 | Kauhaniemi | 356/246 |
| 5,882,494 A | 3/1999 | van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,893,848 A | 4/1999 | Negus | 606/41 |
| 5,893,870 S | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat | 606/170 |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D411,619 S | 6/1999 | Duchon | D24/146 |
| 5,908,416 A | 6/1999 | Costello | 606/9 |
| 5,911,937 A | 6/1999 | Hekal | 264/255 |
| 5,912,134 A | 6/1999 | Shartle | 435/7.24 |

| Patent No. | Date | Inventor | Class |
|---|---|---|---|
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |
| RE36,268 E | 8/1999 | Szuminsky et al. | 205/777.5 |
| 5,931,794 A | 8/1999 | Pitesky | 600/556 |
| 5,933,136 A | 8/1999 | Brown | 345/327 |
| 5,935,075 A | 8/1999 | Casscells | 600/474 |
| 5,938,635 A | 8/1999 | Kuhle | 604/506 |
| 5,938,679 A | 8/1999 | Freeman | 606/181 |
| 5,940,153 A | 8/1999 | Castaneda | 349/58 |
| 5,942,102 A | 8/1999 | Hodges | 205/775 |
| 5,942,189 A | 8/1999 | Wolfbeis | 422/82.08 |
| 5,947,957 A | 9/1999 | Morris | 606/13 |
| 5,951,300 A | 9/1999 | Brown | 434/236 |
| 5,951,492 A | 9/1999 | Douglas | 600/583 |
| 5,951,493 A | 9/1999 | Douglas | 600/583 |
| 5,951,582 A | 9/1999 | Thorne | 606/182 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,957,846 A | 9/1999 | Chiang | 600/447 |
| 5,958,199 A | 9/1999 | Miyamoto | 204/403 |
| 5,959,098 A | 9/1999 | Goldberg | 536/25.3 |
| 5,960,403 A | 9/1999 | Brown | 705/2 |
| 5,961,451 A | 10/1999 | Reber | 600/322 |
| 5,964,718 A | 10/1999 | Duchon | 600/583 |
| 5,965,380 A | 10/1999 | Heller | 435/14 |
| 5,968,063 A | 10/1999 | Chu | 606/185 |
| 5,968,760 A | 10/1999 | Phillips | 435/14 |
| 5,968,836 A | 10/1999 | Matzinger | 436/169 |
| 5,971,941 A | 10/1999 | Simons | 606/573 |
| 5,972,199 A | 10/1999 | Heller | 205/777.5 |
| 5,972,294 A | 10/1999 | Smith | 422/58 |
| 5,972,715 A | 10/1999 | Celentano | 436/164 |
| 5,974,124 A | 10/1999 | Schlueter | 379/106.02 |
| 5,976,085 A | 11/1999 | Kimball | 600/309 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,986,754 A | 11/1999 | Harding | 356/246 |
| 5,993,400 A | 11/1999 | Rincoe | 600/595 |
| 5,993,434 A | 11/1999 | Dev | 604/501 |
| D417,504 S | 12/1999 | Love | D24/169 |
| 5,997,476 A | 12/1999 | Brown | 600/300 |
| 5,997,561 A | 12/1999 | Bocker | 606/182 |
| 5,997,817 A | 12/1999 | Crismore | 422/58 |
| 5,997,818 A | 12/1999 | Hackner | 422/681 |
| 6,001,067 A | 12/1999 | Shults | 600/584 |
| 6,007,497 A | 12/1999 | Huitema | 600/567 |
| D418,602 S | 1/2000 | Prokop | D24/169 |
| 6,014,577 A | 1/2000 | Henning | 600/345 |
| 6,015,392 A | 1/2000 | Douglas | 600/583 |
| 6,018,289 A | 1/2000 | Sekura | 340/309.4 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,022,748 A | 2/2000 | Charych | 436/527 |
| 6,023,629 A | 2/2000 | Tamada | 600/347 |
| 6,023,686 A | 2/2000 | Brown | 705/37 |
| 6,027,459 A | 2/2000 | Shain | 600/573 |
| 6,030,399 A | 2/2000 | Ignotz | 606/167 |
| 6,030,827 A | 2/2000 | Davis | 435/287 |
| 6,030,967 A | 2/2000 | Marui | 514/215 |
| 6,032,059 A | 2/2000 | Henning | 600/345 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons | 422/100 |
| 6,037,178 A | 3/2000 | Leiner | 436/50 |
| 6,041,253 A | 3/2000 | Kost | 604/20 |
| 6,045,567 A | 4/2000 | Taylor | 606/181 |
| 6,046,055 A | 4/2000 | Wolfbeis | 436/172 |
| 6,048,352 A | 4/2000 | Douglas | 606/181 |
| D424,696 S | 5/2000 | Ray | D24/169 |
| 6,056,701 A | 5/2000 | Duchon | 600/583 |
| 6,059,815 A | 5/2000 | Lee | 606/209 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,243 A | 5/2000 | Anderson | 422/82.01 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,070,761 A | 6/2000 | Bloom | 222/81 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,071,294 A | 6/2000 | Simons | 606/181 |
| 6,071,391 A | 6/2000 | Gotoh | 204/403 |
| 6,074,360 A | 6/2000 | Haar et al. | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham et al. | 600/573 |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |
| 6,104,940 A | 8/2000 | Watanabe | 600/345 |
| 6,106,751 A | 8/2000 | Talbot | 264/81 |
| 6,107,083 A | 8/2000 | Collins | 435/288 |
| 6,113,578 A | 9/2000 | Brown | 604/207 |
| 6,117,155 A | 9/2000 | Lee | 606/189 |
| 6,117,630 A | 9/2000 | Reber | 435/4 |
| 6,118,126 A | 9/2000 | Zanzucchi | 250/458.1 |
| 6,119,033 A | 9/2000 | Spigelman | 600/426 |
| 6,119,247 A | | | |
| 6,120,462 A | 9/2000 | Hibner | 600/566 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,126,804 A | 10/2000 | Andresen | 204/601 |
| 6,126,899 A | 10/2000 | Woudenberg | 422/50 |
| 6,129,823 A | 10/2000 | Hughes | 204/403.01 |
| 6,132,449 A | 10/2000 | Lum | 606/181 |
| 6,133,837 A | 10/2000 | Riley | 340/573.1 |
| 6,134,461 A | 10/2000 | Say | 600/345 |
| 6,136,013 A | 10/2000 | Marshall | 606/167 |
| 6,139,562 A | 10/2000 | Mauze | 606/171 |
| 6,143,164 A | 11/2000 | Heller | 600/583 |
| 6,144,837 A | 11/2000 | Quy | 434/307 R |
| 6,144,976 A | 11/2000 | Silva et al. | 708/100 |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman | 606/181 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning | 600/583 |
| 6,156,051 A | 12/2000 | Schraga | 606/181 |
| 6,157,442 A | 12/2000 | Raskas | 356/39 |
| 6,159,147 A | 12/2000 | Lichter | 600/300 |
| 6,159,424 A | 12/2000 | Kauhaniemi et al. | 422/63 |
| 6,161,095 A | 12/2000 | Brown | 705/2 |

| Patent No. | Kind | Date | Inventor | Class |
|---|---|---|---|---|
| 6,162,397 | A | 12/2000 | Jurik | 422/56 |
| 6,162,611 | A | 12/2000 | Heller | 435/14 |
| 6,167,362 | A | 12/2000 | Brown | 703/11 |
| 6,167,386 | A | 12/2000 | Brown | 705/37 |
| 6,168,563 | B1 | 1/2001 | Brown | 600/301 |
| 6,168,957 | B1 | 1/2001 | Matzinger | 436/518 |
| 6,171,325 | B1 | 1/2001 | Mauze | 606/171 |
| 6,172,743 | B1 | 1/2001 | Kley et al. | 356/39 |
| 6,175,752 | B1 | 1/2001 | Say | 600/345 |
| 6,176,847 | B1 | 1/2001 | Humphreys | 604/246 |
| 6,176,865 | B1 | 1/2001 | Mauze | 606/171 |
| 6,177,000 | B1 | 1/2001 | Peterson | 205/777.5 |
| 6,177,931 | B1 | 1/2001 | Alexander | 725/52 |
| 6,183,489 | B1 | 2/2001 | Douglas | 606/181 |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,193,673 | B1 | 2/2001 | Viola | 600/568 |
| 6,193,873 | B1 | 2/2001 | Ohara | 205/792 |
| 6,194,900 | B1 | 2/2001 | Freeman | 324/321 |
| 6,197,040 | B1 | 3/2001 | LeVaughn | 606/182 |
| 6,197,257 | B1 | 3/2001 | Raskas | 422/82.05 |
| 6,200,773 | B1 | 3/2001 | Ouyang | 435/26 |
| 6,203,504 | B1 | 3/2001 | Latterell | 600/576 |
| 6,206,841 | B1 | 3/2001 | Cunningham et al. | 600/584 |
| 6,210,133 | B1 | 4/2001 | Aboul-Hosn | 417/423.1 |
| 6,210,272 | B1 | 4/2001 | Brown | 463/1 |
| 6,210,369 | B1 | 4/2001 | Wilmot | 604/157 |
| 6,210,420 | B1 | 4/2001 | Mauze | 606/182 |
| 6,210,421 | B1 | 4/2001 | Bocker | 606/182 |
| 6,212,417 | B1 | 4/2001 | Ikeda | 204/403.14 |
| 6,214,626 | B1 | 4/2001 | Meller | 436/165 |
| 6,214,804 | B1 | 4/2001 | Felgner | 514/44 |
| 6,218,571 | B1 | 4/2001 | Zheng | 562/61 |
| 6,219,574 | B1 | 4/2001 | Cormier | 604/20 |
| 6,221,023 | B1 | 4/2001 | Matsuba | 600/486 |
| 6,221,238 | B1 | 4/2001 | Grundig | 205/777.5 |
| 6,225,078 | B1 | 5/2001 | Ikeda | 435/25 |
| 6,228,100 | B1 | 5/2001 | Schraga | 606/183 |
| 6,230,051 | B1 | 5/2001 | Cormier | 604/20 |
| 6,230,501 | B1 | 5/2001 | Bailey | 62/51.1 |
| 6,231,531 | B1 | 5/2001 | Lum | 601/46 |
| 6,233,471 | B1 | 5/2001 | Berner | 600/345 |
| 6,233,539 | B1 | 5/2001 | Brown | 703/11 |
| 6,234,772 | B1 | 5/2001 | Wampler | 417/423.12 |
| 6,240,393 | B1 | 5/2001 | Brown | 705/1 |
| D444,235 | S | 6/2001 | Roberts | D24/169 |
| 6,241,862 | B1 | 6/2001 | McAleer | 204/403 |
| 6,242,207 | B1 | 6/2001 | Douglas | 435/25 |
| 6,245,060 | B1 | 6/2001 | Loomis | 606/9 |
| 6,245,215 | B1 | 6/2001 | Douglas | 205/775 |
| 6,246,992 | B1 | 6/2001 | Brown | 705/2 |
| 6,248,065 | B1 | 6/2001 | Brown | 600/300 |
| 6,251,083 | B1 | 6/2001 | Yum | 600/584 |
| 6,251,121 | B1 | 6/2001 | Saadat | 606/180 |
| 6,251,260 | B1 | 6/2001 | Heller | 205/777.5 |
| 6,251,344 | B1 | 6/2001 | Goldstein | 422/123 |
| D444,557 | S | 7/2001 | Levaughn | D24/146 |
| 6,254,831 | B1 | 7/2001 | Barnard | 422/82.08 |
| 6,256,533 | B1 | 7/2001 | Vuzhakov | 604/21 |
| 6,258,111 | B1 | 7/2001 | Ross | 606/181 |
| 6,258,229 | B1 | 7/2001 | Winarta | 204/403 |
| 6,258,254 | B1 | 7/2001 | Miyamoto | 205/777.5 |
| 6,261,241 | B1 | 7/2001 | Burbank | 600/564 |
| 6,261,245 | B1 | 7/2001 | Kawai | 600/576 |
| 6,261,519 | B1 | 7/2001 | Harding | 422/58 |
| 6,264,635 | B1 | 7/2001 | Wampler | 604/151 |
| 6,268,161 | B1 | 7/2001 | Han | 435/14 |
| 6,268,162 | B1 | 7/2001 | Phillips | 435/14 |
| 6,269,314 | B1 | 7/2001 | Iitawaki | 702/23 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,272,364 | B1 | 8/2001 | Kurnik | 600/345 |
| 6,275,717 | B1 | 8/2001 | Gross | 600/345 |
| 6,280,254 | B1 | 8/2001 | Wu | 439/630 |
| 6,281,006 | B1 | 8/2001 | Heller | 435/287.9 |
| 6,283,926 | B1 | 9/2001 | Cunningham et al. | 600/573 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,285,454 | B1 | 9/2001 | Douglas | 356/446 |
| 6,289,254 | B1 | 9/2001 | Shimizu | 700/96 |
| 6,290,683 | B1 | 9/2001 | Erez | 604/273 |
| 6,294,897 | B1 | 9/2001 | Champlin | 320/153 |
| 6,295,506 | B1 | 9/2001 | Heinonen | 702/104 |
| 6,299,578 | B1 | 10/2001 | Kurnik | 600/309 |
| 6,299,596 | B1 | 10/2001 | Ding | 604/96.01 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,104 | B1 | 10/2001 | Cunningham | 600/573 |
| 6,306,152 | B1 | 10/2001 | Verdonk | 606/182 |
| 6,306,347 | B1 | 10/2001 | Mason | 422/58 |
| 6,309,351 | B1 | 10/2001 | Kurnik | 600/309 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa | 600/583 |
| 6,318,970 | B1 | 11/2001 | Backhouse | 417/92 |
| 6,319,210 | B1 | 11/2001 | Douglas | 600/583 |
| 6,322,574 | B1 | 11/2001 | Lloyd | 606/181 |
| 6,322,808 | B1 | 11/2001 | Trautman | 424/448 |
| 6,322,963 | B1 | 11/2001 | Bauer | 435/4 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,332,871 | B1 | 12/2001 | Douglas | 600/583 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,335,203 | B1 | 1/2002 | Patel | 436/169 |
| 6,336,900 | B1 | 1/2002 | Alleckson | 600/485 |
| 6,338,790 | B1 | 1/2002 | Feldman | 205/777.5 |
| 6,346,120 | B1 | 2/2002 | Yamazaki | 623/3.13 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,514 | B1 | 3/2002 | Douglas | 600/583 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri et al. | 606/181 |
| 6,364,890 | B1 | 4/2002 | Lum | 606/181 |
| 6,368,273 | B1 | 4/2002 | Brown | 600/300 |
| 6,375,469 | B1 | 4/2002 | Brown | 434/236 |
| 6,375,627 | B1 | 4/2002 | Mauze | 600/584 |
| 6,379,301 | B1 | 4/2002 | Worthington | 600/309 |
| 6,379,317 | B1 | 4/2002 | Kintzig | 600/573 |
| 6,379,324 | B1 | 4/2002 | Gartstein | 604/22 |
| 6,379,969 | B1 | 4/2002 | Mauze | 436/68 |
| 6,381,577 | B1 | 4/2002 | Brown | 705/2 |
| D456,910 | S | 5/2002 | Clark | D24/225 |
| 6,387,709 | B1 | 5/2002 | Mason | 436/164 |
| 6,391,005 | B1 | 5/2002 | Lum | 604/117 |
| 6,395,227 | B1 | 5/2002 | Kiser | 422/56 |
| 6,398,522 | B2 | 6/2002 | Skill | 417/410.3 |
| 6,398,562 | B1 | 6/2002 | Butler | 439/91 |
| 6,399,394 | B1 | 6/2002 | Dahm | 436/180 |
| 6,402,701 | B1 | 6/2002 | Kaplan | 600/567 |
| 6,402,704 | B1 | 6/2002 | Mcmorrow | 600/576 |
| 6,409,740 | B1 | 6/2002 | Kuhr | 606/182 |
| 6,413,410 | B1 | 7/2002 | Hodges | 205/775 |
| 6,413,411 | B1 | 7/2002 | Pottgen | 205/777.5 |
| 6,415,821 | B2 | 7/2002 | Kamholz | 137/827 |
| 6,420,128 | B1 | 7/2002 | Ouyang | 435/14 |
| 6,421,633 | B1 | 7/2002 | Heinonen | 703/11 |
| 6,423,014 | B1 | 7/2002 | Churchill | 600/587 |
| 6,428,664 | B1 | 8/2002 | Bhullar | 204/403.03 |
| 6,436,055 | B1 | 8/2002 | Roe | 600/584 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,444,115 | B1 | 9/2002 | Hodges | 205/792 |
| 6,447,119 | B1 | 9/2002 | Stewart et al. | 351/212 |
| 6,447,265 | B1 | 9/2002 | Antaki | 417/354 |
| 6,451,040 | B1 | 9/2002 | Purcell | 606/181 |
| 6,453,810 | B1 | 9/2002 | Rossmeisl | 101/123 |

| Patent | Date | Name | Ref |
|---|---|---|---|
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons | 436/63 |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,475,750 B1 | 11/2002 | Han | 435/14 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,891 B2 | 12/2002 | Mason | 422/58 |
| 6,489,133 B2 | 12/2002 | Phillips | 435/14 |
| 6,491,709 B2 | 12/2002 | Sharma | 606/181 |
| 6,491,870 B2 | 12/2002 | Patel | 422/58 |
| 6,494,830 B1 | 12/2002 | Wessel | 600/300 |
| 6,497,845 B1 | 12/2002 | Sacherer | 422/104 |
| 6,501,404 B2 | 12/2002 | Walker | 341/143 |
| 6,501,976 B1 | 12/2002 | Sohrab | 600/347 |
| 6,503,210 B1 | 1/2003 | Hirao | 600/576 |
| 6,503,231 B1 | 1/2003 | Prausnitz | 604/272 |
| 6,503,290 B1 | 1/2003 | Jarosinski | 75/252 |
| 6,503,381 B1 | 1/2003 | Gotoh | 204/403.14 |
| 6,506,165 B1 | 1/2003 | Sweeney | 600/562 |
| 6,506,168 B1 | 1/2003 | Fathallah | 600/578 |
| 6,506,575 B1 | 1/2003 | Knappe | 435/25 |
| 6,508,785 B1 | 1/2003 | Eppstein | 604/113 |
| 6,512,986 B1 | 1/2003 | Harmon | 702/84 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,521,110 B1 | 2/2003 | Hodges | 204/403.14 |
| 6,521,182 B1 | 2/2003 | Shartle | 422/58 |
| 6,527,521 B2 | 3/2003 | Noda | 417/355 |
| 6,527,716 B1 | 3/2003 | Epstein | 600/309 |
| 6,527,778 B2 | 3/2003 | Athanasiou | 606/80 |
| 6,529,377 B1 | 3/2003 | Nelson | 361/699 |
| 6,530,892 B1 | 3/2003 | Kelly | 600/583 |
| 6,530,937 B1 | 3/2003 | Schraga | 606/182 |
| 6,531,322 B1 | 3/2003 | Jurik | 436/95 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,264 B1 | 3/2003 | Cormier et al. | 604/506 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,553,244 B2 | 4/2003 | Lesho | 600/347 |
| 6,554,381 B2 | 4/2003 | Locher | 347/7 |
| 6,555,061 B1 | 4/2003 | Leong | 422/58 |
| D475,136 S | 5/2003 | Taniguchi | D24/165 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,572,822 B2 | 6/2003 | Jurik | 422/56 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki et al. | 205/777.5 |
| 6,576,416 B2 | 6/2003 | Haviland | 435/4 |
| 6,579,690 B1 | 6/2003 | Bonnecaze | 435/14 |
| 6,582,573 B2 | 6/2003 | Douglas | 204/403.1 |
| 6,584,338 B1 | 6/2003 | Van Muiswinkel | 600/419 |
| D477,670 S | 7/2003 | Jurik | D24/225 |
| 6,586,199 B2 | 7/2003 | Ouyang | 435/26 |
| 6,587,705 B1 | 7/2003 | Kim | 600/347 |
| 6,589,260 B1 | 7/2003 | Schmelzeisen-R | 606/181 |
| 6,589,261 B1 | 7/2003 | Abulhaj | 606/181 |
| 6,591,124 B2 | 7/2003 | Sherman et al. | 600/345 |
| 6,591,125 B1 | 7/2003 | Buse | 600/347 |
| 6,592,744 B1 | 7/2003 | Hodges | 205/775 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,599,769 B2 | 7/2003 | Kondo | 438/28 |
| 6,601,534 B2 | 8/2003 | Hebrank | 119/6.8 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,362 B2 | 8/2003 | Lum | 417/53 |
| 6,607,494 B1 | 8/2003 | Fowler | 600/570 |
| 6,607,658 B1 | 8/2003 | Heller | 205/777.5 |
| 6,612,111 B1 | 9/2003 | Hodges | 60/593 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,620,310 B1 | 9/2003 | Ohara | 205/792 |
| 6,623,501 B2 | 9/2003 | Heller | 606/181 |
| 6,626,851 B2 | 9/2003 | Hirao | 600/576 |
| 6,632,349 B1 | 10/2003 | Hodges | 205/792 |
| 6,635,222 B2 | 10/2003 | Kent | 422/22 |
| 6,638,415 B1 | 10/2003 | Hodges | 205/775 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,649,416 B1 | 11/2003 | Kauer | 436/164 |
| 6,650,915 B2 | 11/2003 | Routt | 600/319 |
| 6,652,720 B1 | 11/2003 | Mansouri | 204/403.11 |
| 6,652,734 B1 | 11/2003 | Hodges | 205/777.5 |
| 6,652,814 B1 | 11/2003 | House | 422/104 |
| D484,600 S | 12/2003 | Kaar | D24/169 |
| 6,656,697 B1 | 12/2003 | Ouyang | 435/7.9 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,662,439 B1 | 12/2003 | Bhullar | 29/825 |
| 6,669,669 B2 | 12/2003 | Flaherty | 604/132 |
| 6,671,527 B2 | 12/2003 | Peterson | 600/316 |
| D484,980 S | 1/2004 | Hartwein | D24/165 |
| 6,673,617 B2 | 1/2004 | Patel | 436/8 |
| 6,676,995 B2 | 1/2004 | Dick | 427/286 |
| 6,679,841 B2 | 1/2004 | Bojan | 600/309 |
| 6,679,852 B1 | 1/2004 | Schmelzeisen-Redeker et al. | 600/583 |
| 6,682,933 B2 | 1/2004 | Patel | 436/8 |
| 6,689,411 B2 | 2/2004 | Dick | 427/2.13 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,709,692 B2 | 3/2004 | Sudor | 427/2.1 |
| 6,713,660 B1 | 3/2004 | Roe | 604/361 |
| 6,716,577 B1 | 4/2004 | Yu | 435/6 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |

| Patent | Date | Name | Class |
|---|---|---|---|
| 6,726,818 B2 | 4/2004 | Cui | 204/403.01 |
| 6,729,546 B2 | 5/2004 | Roustaei | 235/462.45 |
| 6,730,494 B1 | 5/2004 | Toranto | 435/28 |
| 6,731,966 B1 | 5/2004 | Spigelman | 600/407 |
| 6,733,493 B2 | 5/2004 | Gruzdev | 606/9 |
| 6,736,777 B2 | 5/2004 | Kim | 600/365 |
| 6,738,654 B2 | 5/2004 | Sohrab | 600/345 |
| 6,740,215 B1 | 5/2004 | Yamamoto | 204/403.14 |
| 6,743,211 B1 | 6/2004 | Prausnitz | 604/239 |
| 6,743,597 B1 | 6/2004 | Guo | 435/14 |
| 6,743,635 B2 | 6/2004 | Neel | 436/95 |
| 6,746,872 B2 | 6/2004 | Zheng | 436/16 |
| 6,749,618 B2 | 6/2004 | Levaughn | 606/182 |
| 6,749,740 B2 | 6/2004 | Liamos | 205/792 |
| 6,749,792 B2 | 6/2004 | Olsen | 264/328.1 |
| 6,749,887 B1 | 6/2004 | Dick | 427/2.13 |
| 6,751,491 B2 | 6/2004 | Lew | 600/345 |
| 6,752,817 B2 | 6/2004 | Flora | 606/181 |
| 6,753,187 B2 | 6/2004 | Cizdziel | 436/169 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grube | 439/66 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/300 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,829,507 B1 | 12/2004 | Lidman | 607/19 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,830,934 B1 | 12/2004 | Hardling | 436/166 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,835,570 B2 | 12/2004 | Patel | 436/8 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,843,902 B1 | 1/2005 | Penner | 205/76 |
| 6,847,451 B2 | 1/2005 | Pugh | 356/436 |
| 6,849,052 B2 | 2/2005 | Uchigaki | 600/584 |
| 6,849,168 B2 | 2/2005 | Crumly | 204/416 |
| 6,849,216 B2 | 2/2005 | Rappin | 264/134 |
| 6,849,456 B2 | 2/2005 | Patel | 436/8 |
| 6,850,790 B2 | 2/2005 | Berner | 600/347 |
| 6,852,119 B1 | 2/2005 | Abulhaj | 606/182 |
| 6,852,212 B2 | 2/2005 | Maxwell | 205/775 |
| 6,852,500 B1 | 2/2005 | Hoss | 435/14 |
| 6,853,854 B1 | 2/2005 | Proniewicz | 600/319 |
| 6,855,243 B2 | 2/2005 | Khan | 205/777.5 |
| 6,856,125 B2 | 2/2005 | Kermani | 324/71.1 |
| 6,856,928 B2 | 2/2005 | Harmon | 702/84 |
| 6,858,015 B2 | 2/2005 | List | 600/583 |
| 6,858,401 B2 | 2/2005 | Phillips | 435/14 |
| 6,859,738 B2 | 2/2005 | Bush | 702/25 |
| 6,862,466 B2 | 3/2005 | Ackerman | 600/347 |
| 6,862,534 B2 | 3/2005 | Sterling | 702/23 |
| 6,863,800 B2 | 3/2005 | Karinka | 205/777.5 |
| 6,863,801 B2 | 3/2005 | Hodges | 205/792 |
| 6,865,408 B1 | 3/2005 | Abbink | 600/310 |
| 6,866,641 B2 | 3/2005 | Marshall | 600/583 |
| 6,866,675 B2 | 3/2005 | Perez | 606/181 |
| 6,866,758 B2 | 3/2005 | Bhullar | 204/403.2 |
| 6,866,822 B1 | 3/2005 | House | 422/82.05 |
| 6,869,418 B2 | 3/2005 | Marano-Ford | 604/192 |
| 6,872,200 B2 | 3/2005 | Mann | 604/890.1 |
| 6,872,297 B2 | 3/2005 | Mansouri | 205/775 |
| 6,872,298 B2 | 3/2005 | Kermani | 205/777.5 |
| 6,872,299 B2 | 3/2005 | Kermani | 205/777.5 |
| 6,872,358 B2 | 3/2005 | Hagen | 422/61 |
| 6,875,208 B2 | 4/2005 | Santini | 604/890.1 |
| 6,875,223 B2 | 4/2005 | Argauer | 606/181 |
| 6,875,327 B1 | 4/2005 | Miyazaki | 204/403.14 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen | 435/6 |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,202 B2 | 5/2005 | Currie | 600/309 |
| 6,887,239 B2 | 5/2005 | Elstrom | 606/41 |
| 6,887,253 B2 | 5/2005 | Schraga | 606/181 |
| 6,887,254 B1 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor et al. | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |

| Patent | Date | Inventor | Class |
|---|---|---|---|
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,874 B1 | 7/2005 | Hatch | 606/365 |
| 6,918,901 B1 | 7/2005 | Theeuwes | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,977,722 B2 | 12/2005 | Wohlstadter et al. | 356/246 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin | 250/573 |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D522,656 S | 6/2006 | Orr | D24/169 |
| D523,555 S | 6/2006 | Loerwald | D24/146 |
| 7,056,425 B2 | 6/2006 | Hasegawa | 204/403.04 |

| Patent | Date | Name | Ref |
|---|---|---|---|
| 7,056,495 B2 | 6/2006 | Roser | 424/45 |
| 7,058,437 B2 | 6/2006 | Buse | 600/347 |
| 7,059,352 B2 | 6/2006 | Bohm | 137/828 |
| 7,060,059 B2 | 6/2006 | Keith | 604/504 |
| 7,060,168 B2 | 6/2006 | Taniike | 204/403.04 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.04 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,079,252 B1 | 7/2006 | Debreezeny | 356/451 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,006 B2 | 9/2006 | Shraga | 606/182 |
| 7,107,253 B1 | 9/2006 | Sumner | 706/6 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,113,172 B2 | 9/2006 | Hohl | 345/168 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/366 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorczyk | 205/792 |
| 7,144,496 B2 | 12/2006 | Meserol | 205/775 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem | 435/6 |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,199 B2 | 2/2007 | Berner | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Monfre et al. | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erickson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman | 29/831 |
| 7,226,414 B2 | 6/2007 | Ballerstadt | 600/365 |
| 7,226,461 B2 | 6/2007 | Boecker | 606/181 |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Freeman | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,138 B2 | 7/2007 | Reghabi | 600/365 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |

| Patent | Date | Name | Class |
|---|---|---|---|
| 7,251,513 B2 | 7/2007 | Kondoh | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen | 606/181 |
| 7,291,256 B2 | 11/2007 | Teodorczyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |
| 7,297,122 B2 | 11/2007 | Boecker | 600/583 |
| 7,297,151 B2 | 11/2007 | Boccker | 606/181 |
| 7,297,152 B2 | 11/2007 | Fukuzawa | 606/181 |
| 7,297,241 B2 | 11/2007 | Kontschieder | 204/403.14 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/310 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,324,012 B2 | 1/2008 | Mann | 340/870.07 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.01 |
| 7,347,925 B2 | 3/2008 | Hsich | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Shartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,270 B2 | 5/2008 | Azarnia | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |

| Patent/Pub No. | Date | Name | Class |
|---|---|---|---|
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0018353 A1 | 8/2001 | Ishigaki | 455/566 |
| 2001/0027328 A1 | 10/2001 | Lum | 606/186 |
| 2001/0031931 A1 | 10/2001 | Cunningham | 600/573 |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016606 A1 | 2/2002 | Moerman | 606/181 |
| 2002/0016923 A1 | 2/2002 | Knaus | 713/200 |
| 2002/0019606 A1 | 2/2002 | Lebel | 604/66 |
| 2002/0019747 A1 | 2/2002 | Ware | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum et al. | 606/183 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan | 600/573 |
| 2002/0103499 A1 | 8/2002 | Perez | 606/182 |
| 2002/0120216 A1 | 8/2002 | Fritz | 600/573 |
| 2002/0120261 A1 | 8/2002 | Morris | 606/41 |
| 2002/0123335 A1 | 9/2002 | Luna | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069509 A1 | 4/2003 | Matzinger et al. | 600/504 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman | 73/304 C |
| 2003/0139653 A1 | 7/2003 | Manser | 600/300 |
| 2003/0143113 A2 | 7/2003 | Yuzjakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149371 A1 | 8/2003 | Erickson | 600/583 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191376 A1 | 10/2003 | Samuels | 600/309 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |

| Pub. No. | Date | Name | Class |
|---|---|---|---|
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0210811 A1 | 11/2003 | Dubowsky | 382/128 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0026244 A1 | 2/2004 | Hodges | 204/409 |
| 2004/0030353 A1 | 2/2004 | Schmelzeisen-R | 606/181 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0069657 A1 | 4/2004 | Hodges | 205/787 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/6 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs et al. | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |

| Pub. No. | Date | Inventor | Class |
|---|---|---|---|
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403.01 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/43 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode | 600/365 |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara et al. | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Shraga | 606/182 |
| 2005/0038465 A1 | 2/2005 | Shraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowicz | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130250 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |

| | | | | | | |
|---|---|---|---|---|---|---|
| 2005/0143771 A1 | 6/2005 | Stout ............... 606/181 | 2005/0234488 A1 | 10/2005 | Allen ............... 606/181 |
| 2005/0145490 A1 | 7/2005 | Shinno ............. 204/403 | 2005/0234489 A1 | 10/2005 | Allen ............... 606/181 |
| 2005/0145491 A1 | 7/2005 | Amano ............. 204/403 | 2005/0234490 A1 | 10/2005 | Allen ............... 606/181 |
| 2005/0145520 A1 | 7/2005 | Ilo ................... 206/365 | 2005/0234491 A1 | 10/2005 | Allen ............... 606/181 |
| 2005/0149088 A1 | 7/2005 | Fukuda ............ 606/181 | 2005/0234492 A1 | 10/2005 | Tsai ................. 606/181 |
| 2005/0149089 A1 | 7/2005 | Trissel ............. 606/181 | 2005/0234494 A1 | 10/2005 | Conway ........... 606/181 |
| 2005/0149090 A1 | 7/2005 | Morita et al. .... 606/181 | 2005/0234495 A1 | 10/2005 | Schraga ........... 606/181 |
| 2005/0150762 A1 | 7/2005 | Butters ............ 204/403 | 2005/0235060 A1 | 10/2005 | Brown .............. 709/224 |
| 2005/0150763 A1 | 7/2005 | Butters ............ 204/403 | 2005/0239154 A1 | 10/2005 | Feldman ........... 435/14 |
| 2005/0154277 A1 | 7/2005 | Ting ................ 600/407 | 2005/0239156 A1 | 10/2005 | Drucker ........... 435/14 |
| 2005/0154374 A1 | 7/2005 | Hunter ............. 604/890 | 2005/0239194 A1 | 10/2005 | Takahashi ........ 435/287.2 |
| 2005/0154410 A1 | 7/2005 | Conway ........... 606/181 | 2005/0240090 A1 | 10/2005 | Ruchti .............. 600/316 |
| 2005/0154616 A1 | 7/2005 | Iliff .................. 705/3 | 2005/0240119 A1 | 10/2005 | Draudt .............. 600/583 |
| 2005/0158850 A1 | 7/2005 | Kubo ............... 435/287.2 | 2005/0240207 A1 | 10/2005 | Marshall .......... 606/181 |
| 2005/0159656 A1 | 7/2005 | Hockersmith .... 600/315 | 2005/0240778 A1 | 10/2005 | Saito ................ 713/186 |
| 2005/0159768 A1 | 7/2005 | Boehm ............. 606/182 | 2005/0245798 A1 | 11/2005 | Yamaguchi ....... 600/345 |
| 2005/0164322 A1 | 7/2005 | Heller .............. 435/14 | 2005/0245843 A1 | 11/2005 | Day ................. 600/583 |
| 2005/0164329 A1 | 7/2005 | Wallace-Davis .. 435/25 | 2005/0245844 A1 | 11/2005 | Mace ............... 600/583 |
| 2005/0165285 A1 | 7/2005 | Iliff .................. 600/300 | 2005/0245845 A1 | 11/2005 | Roe .................. 600/583 |
| 2005/0165393 A1 | 7/2005 | Eppstein .......... 606/41 | 2005/0245954 A1 | 11/2005 | Roe .................. 606/181 |
| 2005/0165622 A1 | 7/2005 | Neel ................. 705/2 | 2005/0245955 A1 | 11/2005 | Schraga ........... 606/181 |
| 2005/0169810 A1 | 8/2005 | Hagen .............. 422/102 | 2005/0246436 A1 | 11/2005 | Day ................. 600/583 |
| 2005/0169961 A1 | 8/2005 | Hunter ............. 424/423 | 2005/0256534 A1 | 11/2005 | Alden .............. 606/182 |
| 2005/0170448 A1 | 8/2005 | Burson ............ 435/14 | 2005/0258035 A1 | 11/2005 | Harding ........... 204/403.01 |
| 2005/0171567 A1 | 8/2005 | DeHart ............ 606/181 | 2005/0258036 A1 | 11/2005 | Harding ........... 204/403.01 |
| 2005/0172021 A1 | 8/2005 | Brown ............. 709/224 | 2005/0258050 A1 | 11/2005 | Harding ........... 205/775 |
| 2005/0172022 A1 | 8/2005 | Brown ............. 709/224 | 2005/0265094 A1 | 12/2005 | Harding ........... 365/203 |
| 2005/0173245 A1 | 8/2005 | Feldman .......... 204/403.01 | 2005/0276133 A1 | 12/2005 | Harding ........... 365/203 |
| 2005/0173246 A1 | 8/2005 | Hodges ............ 204/403.11 | 2005/0278945 A1 | 12/2005 | Feldman ........... 29/830 |
| 2005/0175509 A1 | 8/2005 | Nakaminami .... 422/82.03 | 2005/0279631 A1 | 12/2005 | Celentano ........ 204/403 |
| 2005/0176084 A1 | 8/2005 | Burkoth ........... 435/14 | 2005/0279647 A1 | 12/2005 | Beaty ............... 205/792 |
| 2005/0176133 A1 | 8/2005 | Miyashita ........ 435/287.1 | 2005/0283094 A1 | 12/2005 | Thym ............... 600/583 |
| 2005/0176153 A1 | 8/2005 | O'hara ............. 436/70 | 2005/0284110 A1 | 12/2005 | Lang ................ 53/473 |
| 2005/0177071 A1 | 8/2005 | Nakayama ....... 600/583 | 2005/0284757 A1 | 12/2005 | Allen ............... 204/400 |
| 2005/0177201 A1 | 8/2005 | Freeman .......... 607/46 | 2005/0287620 A1 | 12/2005 | Heller .............. 435/14 |
| 2005/0177398 A1 | 8/2005 | Watanabe ......... 705/3 | 2005/0288637 A1 | 12/2005 | Kuhr ................ 604/204 |
| 2005/0178218 A1 | 8/2005 | Montagu .......... 73/864.34 | 2005/0288698 A1 | 12/2005 | Matsumoto ...... 606/181 |
| 2005/0181010 A1 | 8/2005 | Hunter ............. 424/423 | 2005/0288699 A1 | 12/2005 | Schraga ........... 606/181 |
| 2005/0181497 A1 | 8/2005 | Saito ................ 435/287.1 | 2006/0000549 A1 | 1/2006 | Lang ................ 156/320 |
| 2005/0182307 A1 | 8/2005 | Currie .............. 600/300 | 2006/0003398 A1 | 1/2006 | Heller .............. 435/14 |
| 2005/0187439 A1 | 8/2005 | Blank ............... 600/310 | 2006/0004270 A1 | 1/2006 | Bedard ............. 600/316 |
| 2005/0187444 A1 | 8/2005 | Hubner ............ 600/322 | 2006/0004271 A1 | 1/2006 | Peyser ............. 600/362 |
| 2005/0192488 A1 | 9/2005 | Bryenton ......... 600/301 | 2006/0004272 A1 | 1/2006 | Shah ................ 600/365 |
| 2005/0196821 A1 | 9/2005 | Monfre ............ 435/14 | 2006/0006574 A1 | 1/2006 | Lang ................ 264/165 |
| 2005/0197666 A1 | 9/2005 | Raney .............. 606/181 | 2006/0008389 A1 | 1/2006 | Sacherer .......... 422/102 |
| 2005/0201897 A1 | 9/2005 | Zimmer ........... 422/82.05 | 2006/0015129 A1 | 1/2006 | Shahrokni ........ 606/181 |
| 2005/0202567 A1 | 9/2005 | Zanzucchi ........ 436/95 | 2006/0016698 A1 | 1/2006 | Lee .................. 205/777.5 |
| 2005/0203358 A1 | 9/2005 | Monfre ............ 600/331 | 2006/0020228 A1 | 1/2006 | Fowler ............. 600/583 |
| 2005/0203364 A1 | 9/2005 | Monfre ............ 600/365 | 2006/0024774 A1 | 2/2006 | Zocchi ............. 435/14 |
| 2005/0204939 A1 | 9/2005 | Krejci .............. 101/129 | 2006/0025662 A1 | 2/2006 | Buse ................ 600/347 |
| 2005/0205136 A1 | 9/2005 | Freeman .......... 137/554 | 2006/0029979 A1 | 2/2006 | Bai .................. 435/7.1 |
| 2005/0205422 A1 | 9/2005 | Moser .............. 204/403.06 | 2006/0029991 A1 | 2/2006 | Hagino ............. 435/14 |
| 2005/0205816 A1 | 9/2005 | Hayenga .......... 251/61.1 | 2006/0030028 A1 | 2/2006 | Nakaminami .... 435/287.2 |
| 2005/0209515 A1 | 9/2005 | Hockersmith .... 600/316 | 2006/0030050 A1 | 2/2006 | Milne .............. 436/67 |
| 2005/0209564 A1 | 9/2005 | Bonner ............ 604/173 | 2006/0030761 A1 | 2/2006 | Raskas ............. 600/316 |
| 2005/0209625 A1 | 9/2005 | Chan ................ 606/181 | 2006/0030788 A1 | 2/2006 | Wong ............... 600/583 |
| 2005/0211571 A1 | 9/2005 | Schulein .......... 205/777.5 | 2006/0034728 A1 | 2/2006 | Kloepfer .......... 422/68.1 |
| 2005/0211572 A1 | 9/2005 | Buck ................ 205/778 | 2006/0037859 A1 | 2/2006 | Hodges ............ 204/400 |
| 2005/0214881 A1 | 9/2005 | Azarnia ............ 435/7.92 | 2006/0040333 A1 | 2/2006 | Zocchi ............. 435/14 |
| 2005/0214892 A1 | 9/2005 | Kovatchev ....... 435/25 | 2006/0047220 A1 | 3/2006 | Sakata ............. 600/583 |
| 2005/0215871 A1 | 9/2005 | Feldman .......... 600/309 | 2006/0047294 A1 | 3/2006 | Mori ................ 606/181 |
| 2005/0215891 A1 | 9/2005 | Berner ............. 600/347 | 2006/0052723 A1 | 3/2006 | Roe .................. 600/583 |
| 2005/0215923 A1 | 9/2005 | Wiegel ............. 600/573 | 2006/0052724 A1 | 3/2006 | Roe .................. 600/583 |
| 2005/0215925 A1 | 9/2005 | Chan ................ 600/583 | 2006/0052809 A1 | 3/2006 | Karbowniczek .. 606/181 |
| 2005/0216046 A1 | 9/2005 | Yeoh ................ 606/181 | 2006/0052810 A1 | 3/2006 | Freeman .......... 606/181 |
| 2005/0218024 A1 | 10/2005 | Lang ................ 206/438 | 2006/0058827 A1 | 3/2006 | Sakata ............. 606/181 |
| 2005/0221276 A1 | 10/2005 | Rozakis ........... 435/4 | 2006/0058828 A1 | 3/2006 | Shi .................. 606/181 |
| 2005/0221470 A1 | 10/2005 | Matsumoto ...... 435/287.1 | 2006/0062852 A1 | 3/2006 | Holmes ............ 424/484 |
| 2005/0222599 A1 | 10/2005 | Czernecki ........ 606/182 | 2006/0063988 A1 | 3/2006 | Schurman ........ 600/316 |
| 2005/0227372 A1 | 10/2005 | Khan ................ 436/514 | 2006/0064035 A1 | 3/2006 | Wang ............... 600/583 |
| 2005/0228242 A1 | 10/2005 | Kawamura ....... 600/300 | 2006/0072670 A1 | 4/2006 | Hasegawa ........ 204/403.01 |
| 2005/0228883 A1 | 10/2005 | Brown ............. 709/224 | 2006/0079739 A1 | 4/2006 | Chen Wang ..... 600/300 |
| 2005/0230252 A1 | 10/2005 | Tsai ................. 204/450 | 2006/0079810 A1 | 4/2006 | Patel ................ 600/583 |
| 2005/0230253 A1 | 10/2005 | Marquant ......... 204/451 | 2006/0079811 A1 | 4/2006 | Roe .................. 600/583 |
| 2005/0232813 A1 | 10/2005 | Karmali ........... 422/58 | 2006/0079920 A1 | 4/2006 | Schraga ........... 606/181 |
| 2005/0232815 A1 | 10/2005 | Ruhl ................ 422/66 | 2006/0081469 A1 | 4/2006 | Lee .................. 204/403.02 |
| 2005/0234368 A1 | 10/2005 | Wong ............... 600/583 | 2006/0085020 A1 | 4/2006 | Freeman .......... 606/181 |
| 2005/0234486 A1 | 10/2005 | Allen ............... 606/181 | 2006/0085137 A1 | 4/2006 | Bartkowiak ...... 702/19 |
| 2005/0234487 A1 | 10/2005 | Shi .................. 600/181 | 2006/0086624 A1 | 4/2006 | Tapsak ............. 205/775 |

| Publication No. | Date | Name | Class |
|---|---|---|---|
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0101980 A1 | 5/2006 | Alden | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/262 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234263 A1 | 10/2006 | Light | 435/6 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna et al. | 606/181 |
| 2006/0266644 A1 | 11/2006 | Pugh | 204/400 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0279431 A1 | 12/2006 | Bakarania | 340/870.02 |
| 2006/0281187 A1 | 12/2006 | Emery | 436/169 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |

| Pub. No. | Date | Inventor | Class |
|---|---|---|---|
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata et al. | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0129618 A1 | 6/2007 | Goldberger | 600/345 |
| 2007/0129650 A1 | 6/2007 | Freeman | 600/583 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Freeman | 600/583 |
| 2007/0142776 A9 | 6/2007 | Kovelman | 604/131 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Boecker | 600/583 |
| 2007/0173742 A1 | 7/2007 | Freeman et al. | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 600/583 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe et al. | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/181 |
| 2007/0233167 A1 | 10/2007 | Weiss | 606/182 |
| 2007/0233395 A1 | 10/2007 | Neel | 702/19 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |

| Publication No. | Date | Name | Ref |
|---|---|---|---|
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer, II | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0255598 A1 | 10/2008 | LeVaughn et al. | 606/183 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |

| | | | | | | |
|---|---|---|---|---|---|---|
| 2008/0277291 A1 | 11/2008 | Heller | 205/777.5 | DE | 10245721 | | 12/2003 |
| 2008/0277292 A1 | 11/2008 | Heller | 205/777.5 | DE | 10361560 | A1 | 7/2005 |
| 2008/0277293 A1 | 11/2008 | Heller | 205/777.5 | EP | 0112498 | A2 | 7/1984 |
| 2008/0277294 A1 | 11/2008 | Heller | 205/777.5 | EP | 137975 | A2 | 4/1985 |
| 2008/0286149 A1 | 11/2008 | Roc | 422/58 | EP | 0160768 | | 11/1985 |
| 2008/0294068 A1 | 11/2008 | Briggs et al. | 600/583 | EP | 0199484 | A2 | 10/1986 |
| 2008/0300614 A1 | 12/2008 | Freeman | 606/181 | EP | 0254246 | | 1/1988 |
| 2008/0318193 A1 | 12/2008 | Alvarez-Icaza | 434/262 | EP | 0289 269 | | 11/1988 |
| 2008/0319284 A1 | 12/2008 | Alvarez-Icaza | 600/309 | EP | 0317847 | A1 | 5/1989 |
| 2008/0319291 A1 | 12/2008 | Freeman | 600/347 | EP | 0320109 | | 6/1989 |
| 2009/0005664 A1 | 1/2009 | Freeman | 600/347 | EP | 0364208 | A1 | 4/1990 |
| 2009/0020438 A1 | 1/2009 | Hodges | 205/782 | EP | 0170375 | | 5/1990 |
| 2009/0024009 A1 | 1/2009 | Freeman | 600/309 | EP | 0136362 | | 12/1990 |
| 2009/0024059 A1 | 1/2009 | Hoerauf et al. | 600/583 | EP | 0449525 | | 10/1991 |
| 2009/0026075 A1 | 1/2009 | Harding | 204/403.14 | EP | 0453283 | | 10/1991 |
| 2009/0026091 A1 | 1/2009 | Harding | 205/777.5 | EP | 0263948 | | 2/1992 |
| 2009/0027040 A1 | 1/2009 | Kermani | 324/123 | EP | 0449147 | A2 | 8/1992 |
| 2009/0029479 A1 | 1/2009 | Docherty | 436/149 | EP | 0530994 | | 3/1993 |
| 2009/0043177 A1 | 2/2009 | Milledge | 600/309 | EP | 0374355 | | 6/1993 |
| 2009/0043183 A1 | 2/2009 | Kermani | 600/365 | EP | 0351891 | | 9/1993 |
| 2009/0048536 A1 | 2/2009 | Freeman | 606/181 | EP | 0593096 | | 4/1994 |
| 2009/0054813 A1 | 2/2009 | Freeman | 600/584 | EP | 0630609 | A2 | 12/1994 |
| 2009/0057146 A1 | 3/2009 | Teodorczyk | 204/403.01 | EP | 0415388 | | 5/1995 |
| 2009/0069716 A1 | 3/2009 | Freeman | 600/583 | EP | 0654659 | | 5/1995 |
| 2009/0084687 A1 | 4/2009 | Chatelier | 205/792 | EP | 0505494 | | 7/1995 |
| 2009/0105572 A1 | 4/2009 | Malecha | 600/365 | EP | 0662367 | A1 | 7/1995 |
| 2009/0105573 A1 | 4/2009 | Malecha | 600/365 | EP | 0359831 | | 8/1995 |
| 2009/0112123 A1 | 4/2009 | Freeman | 600/583 | EP | 0471986 | | 10/1995 |
| 2009/0112155 A1 | 4/2009 | Zhao | 604/67 | EP | 0368474 | | 12/1995 |
| 2009/0112180 A1 | 4/2009 | Krulevitch | 604/506 | EP | 0461601 | | 12/1995 |
| 2009/0112185 A1 | 4/2009 | Krulevitch | 604/523 | EP | 0429076 | | 1/1996 |
| 2009/0124932 A1 | 5/2009 | Freeman | 606/181 | EP | 0552223 | | 7/1996 |
| 2009/0131829 A1 | 5/2009 | Freeman | 600/583 | EP | 0735363 | | 10/1996 |
| 2009/0131830 A1 | 5/2009 | Freeman | 600/583 | EP | 0505504 | | 3/1997 |
| 2009/0131964 A1 | 5/2009 | Freeman | 606/181 | EP | 0777123 | | 6/1997 |
| 2009/0131965 A1 | 5/2009 | Freeman | 606/181 | EP | 0406304 | | 8/1997 |
| 2009/0137930 A1 | 5/2009 | Freeman | 600/583 | EP | 0537761 | | 8/1997 |
| 2009/0138032 A1 | 5/2009 | Freeman | 606/181 | EP | 0795601 | | 9/1997 |
| 2009/0139300 A1 | 6/2009 | Pugh | 73/1.36 | EP | 0562370 | | 11/1997 |
| 2009/0184004 A1 | 7/2009 | Chatelier | 205/777.5 | EP | 0415393 | | 12/1997 |
| 2009/0187351 A1 | 7/2009 | Orr | 702/19 | EP | 0823239 | | 2/1998 |
| 2009/0192410 A1 | 7/2009 | Freeman | 600/583 | EP | 0560336 | | 5/1998 |
| 2009/0192411 A1 | 7/2009 | Freeman | 600/583 | EP | 0878 708 | | 11/1998 |
| 2009/0196580 A1 | 8/2009 | Freeman | 386/124 | EP | 0505475 | | 3/1999 |
| 2009/0204025 A1 | 8/2009 | Marsot | 600/573 | EP | 0898936 | A2 | 3/1999 |
| 2009/0216100 A1 | 8/2009 | Ebner | 600/347 | EP | 0901018 | | 3/1999 |
| 2009/0237262 A1 | 9/2009 | Smith | 340/634 | EP | 0470649 | | 6/1999 |
| 2009/0240127 A1 | 9/2009 | Ray | 600/365 | EP | 0951939 | A2 | 10/1999 |
| 2009/0247838 A1 | 10/2009 | Cummings | 600/309 | EP | 0847447 | | 11/1999 |
| 2009/0247982 A1 | 10/2009 | Kurlevitch | 604/500 | EP | 0964059 | | 12/1999 |
| 2009/0259146 A1 | 10/2009 | Freeman | 600/583 | EP | 0964060 | | 12/1999 |
| 2009/0280551 A1 | 11/2009 | Cardosi | 435/190 | EP | 0969097 | | 1/2000 |
| 2009/0281457 A1 | 11/2009 | Faulkner | 600/583 | EP | 0985376 | A1 | 3/2000 |
| 2009/0281458 A1 | 11/2009 | Faulkner | 600/583 | EP | 1021950 | | 7/2000 |
| 2009/0281459 A1 | 11/2009 | Faulkner | 600/583 | EP | 0894869 | | 2/2001 |
| 2009/0301899 A1 | 12/2009 | Hodges | 205/777.5 | EP | 1074832 | | 2/2001 |
| 2009/0302872 A1 | 12/2009 | Haggett | 324/715 | EP | 1093854 | | 4/2001 |
| 2009/0302873 A1 | 12/2009 | Haggett | 324/724 | EP | 1101443 | A2 | 5/2001 |
| 2009/0322630 A1 | 12/2009 | Friman | 343/720 | EP | 1114995 | | 7/2001 |
| 2009/0325307 A1 | 12/2009 | Haggett | 436/150 | EP | 0736607 | | 8/2001 |
| 2010/0016700 A1 | 1/2010 | Sieh | 600/365 | EP | 0874984 | | 11/2001 |
| 2010/0018878 A1 | 1/2010 | Davies | 205/782 | EP | 1157660 | | 11/2001 |
| 2010/0030110 A1 | 2/2010 | Choi | 600/583 | EP | 0730037 | | 12/2001 |
| 2010/0041084 A1 | 2/2010 | Stephens | 435/14 | EP | 0636879 | | 1/2002 |
| | | | | EP | 01174083 | | 1/2002 |
| | FOREIGN PATENT DOCUMENTS | | | EP | 0851224 | | 3/2002 |
| DE | 4212315 A1 | 10/1993 | | EP | 0759553 | | 5/2002 |
| DE | 4320347 | 12/1994 | | EP | 0856586 | | 5/2002 |
| DE | 4344452 | 6/1995 | | EP | 0817809 | | 7/2002 |
| DE | 4420232 | 12/1995 | | EP | 0872728 | | 7/2002 |
| DE | 29800611 U | 7/1998 | | EP | 0795748 | | 8/2002 |
| DE | 19819407 | 11/1999 | | EP | 0685737 | | 9/2002 |
| DE | 20009475 | 10/2000 | | EP | 0958495 | | 11/2002 |
| DE | 29824204 | 10/2000 | | EP | 0937249 | | 12/2002 |
| DE | 10032042 | 1/2002 | | EP | 1337182 | | 8/2003 |
| DE | 10057832 | 2/2002 | | EP | 0880692 | | 1/2004 |
| DE | 10057832 C1 | 2/2002 | | EP | 01374770 | | 1/2004 |
| DE | 10142232 | 3/2003 | | EP | 1404232 | | 4/2004 |
| DE | 10208575 C1 | 8/2003 | | EP | 1404233 | | 4/2004 |

| | | | | | |
|---|---|---|---|---|---|
| EP | 1246688 | 5/2004 | WO | WO 00/09184 | 2/2000 |
| EP | 1502614 | 2/2005 | WO | WO 00/11578 | 3/2000 |
| EP | 1643908 | 4/2006 | WO | WO 00/15103 | 3/2000 |
| EP | 1790288 | 5/2007 | WO | WO 00/17799 | 3/2000 |
| EP | 1921992 | 5/2008 | WO | WO 00/17800 | 3/2000 |
| EP | 2039294 | 5/2009 | WO | WO 00/18293 | 4/2000 |
| FR | 2555432 | 5/1985 | WO | WO 00/19346 | 4/2000 |
| FR | 2622457 | 11/1987 | WO | WO 00/20626 | 4/2000 |
| GB | 1558111 | 12/1979 | WO | WO00/29577 | 5/2000 |
| GB | 2168815 | 6/1986 | WO | WO 00/30186 | 5/2000 |
| GB | 2331936 | 6/1999 | WO | WO 00/32097 | 6/2000 |
| GB | 2335860 | 10/1999 | WO | WO 00/32098 | 6/2000 |
| GB | 2335990 | 10/1999 | WO | WO 00/33236 | 6/2000 |
| JP | HEI 4 194660 | 7/1992 | WO | WO 00/39914 | 7/2000 |
| JP | 1996010208 | 12/1992 | WO | WO 00/42422 | 7/2000 |
| JP | 9-276235 | 10/1997 | WO | WO 00/44084 | 7/2000 |
| JP | 1014906 | 1/1998 | WO | WO00/46854 | 8/2000 |
| JP | 2000-116768 | 4/2000 | WO | WO 00/50771 | 8/2000 |
| WO | WO 80/01389 | 7/1980 | WO | WO00/55915 | 9/2000 |
| WO | WO 85/04089 | 9/1985 | WO | WO 00/60340 | 10/2000 |
| WO | WO 86/07632 | 12/1985 | WO | WO 00/64022 | 10/2000 |
| WO | WO86/05966 | 10/1986 | WO | WO 00/67245 | 11/2000 |
| WO | WO 91/09139 | 6/1991 | WO | WO 00/67268 | 11/2000 |
| WO | WO92/03099 | 3/1992 | WO | WO 00/72452 | 11/2000 |
| WO | WO92/06971 | 4/1992 | WO | WO 01/00090 | 1/2001 |
| WO | WO92/07263 | 4/1992 | WO | WO 01/15807 A1 | 3/2001 |
| WO | WO92/07468 | 5/1992 | WO | WO 01/16578 A1 | 3/2001 |
| WO | WO93/00044 | 1/1993 | WO | WO 01/75433 | 3/2001 |
| WO | WO 93/02720 | 2/1993 | WO | WO 01/23885 | 4/2001 |
| WO | WO 93/06979 | 4/1993 | WO | WO 01/25775 | 4/2001 |
| WO | WO93/09723 | 5/1993 | WO | WO 01/26813 | 4/2001 |
| WO | WO 93/12726 | 7/1993 | WO | WO01/29037 | 4/2001 |
| WO | WO 93/25898 | 12/1993 | WO | WO 01/33216 | 5/2001 |
| WO | WO 94/27140 | 11/1994 | WO | WO 01/34029 | 5/2001 |
| WO | WO 94/29703 | 12/1994 | WO | WO 01/36955 | 5/2001 |
| WO | WO 94/29704 | 12/1994 | WO | WO 01/37174 | 5/2001 |
| WO | WO 94/29731 | 12/1994 | WO | WO 01/45014 A1 | 6/2001 |
| WO | WO 95/00662 | 1/1995 | WO | WO 01/40788 | 7/2001 |
| WO | WO 95/06240 | 3/1995 | WO | WO 01/57510 | 8/2001 |
| WO | WO 95/10223 | 4/1995 | WO | WO 01/63271 | 8/2001 |
| WO | WO95/12583 | 5/1995 | WO | WO 01/64105 | 9/2001 |
| WO | WO 95/22597 | 8/1995 | WO | WO 01/66010 | 9/2001 |
| WO | WO96/14799 | 5/1996 | WO | WO 01/69505 | 9/2001 |
| WO | WO 96/30431 | 10/1996 | WO | WO 01/72220 A1 | 10/2001 |
| WO | WO96/37148 | 11/1996 | WO | WO 01/72225 | 10/2001 |
| WO | WO 97/02359 | 1/1997 | WO | WO 01/73124 | 10/2001 |
| WO | WO 97/02487 | 1/1997 | WO | WO 01/73395 | 10/2001 |
| WO | WO 97/11883 | 4/1997 | WO | WO 01/89691 | 11/2001 |
| WO | WO 97/18464 | 5/1997 | WO | WO 01/95806 | 12/2001 |
| WO | WO97/28741 | 8/1997 | WO | WO 02/00101 | 1/2002 |
| WO | WO 97/30344 | 8/1997 | WO | WO 02/02796 | 1/2002 |
| WO | WO 97/42882 | 11/1997 | WO | WO 02/08750 | 1/2002 |
| WO | WO 97/42888 | 11/1997 | WO | WO 02/08753 | 1/2002 |
| WO | WO 97/45720 | 12/1997 | WO | WO 02/08950 | 1/2002 |
| WO | WO 98/03431 | 1/1998 | WO | WO 02/18940 | 3/2002 |
| WO | WO98/14436 | 4/1998 | WO | WO 02/21317 | 3/2002 |
| WO | WO 98/19159 | 5/1998 | WO | WO 02/25551 | 3/2002 |
| WO | WO98/19609 | 5/1998 | WO | WO 02/32559 | 4/2002 |
| WO | WO 98/20332 | 5/1998 | WO | WO 02/41227 | 5/2002 |
| WO | WO 98/20348 | 5/1998 | WO | WO 02/41779 | 5/2002 |
| WO | WO98/20867 | 5/1998 | WO | WO 02/44948 | 6/2002 |
| WO | WO 98/24366 | 6/1998 | WO | WO 02/49507 | 6/2002 |
| WO | WO 98 24373 | 6/1998 | WO | WO02/49507 | 6/2002 |
| WO | WO 98/35225 | 8/1998 | WO | WO 02/056769 | 7/2002 |
| WO | WO98/45276 | 10/1998 | WO | WO 02/059734 | 8/2002 |
| WO | WO 99/03584 | 1/1999 | WO | WO 02/069791 | 9/2002 |
| WO | WO 99/05966 | 2/1999 | WO | WO 02/077638 | 10/2002 |
| WO | WO99/07295 | 2/1999 | WO | WO 02/100251 | 12/2002 |
| WO | WO 99/07431 | 2/1999 | WO | WO 02/100252 | 12/2002 |
| WO | WO 99/62576 | 3/1999 | WO | WO 02/100253 | 12/2002 |
| WO | WO 99/17854 | 4/1999 | WO | WO 02/100254 | 12/2002 |
| WO | WO 99/18532 | 4/1999 | WO | WO 02/100460 | 12/2002 |
| WO | WO 99/19507 | 4/1999 | WO | WO 02/100461 | 12/2002 |
| WO | WO 99/19717 | 4/1999 | WO | WO 02/101343 | 12/2002 |
| WO | WO 99/27483 | 6/1999 | WO | WO 02/101359 | 12/2002 |
| WO | WO 99/27852 | 6/1999 | WO | WO 03/000321 | 1/2003 |
| WO | WO 99/13100 | 12/1999 | WO | WO 03/023389 | 3/2003 |
| WO | WO 99/64580 | 12/1999 | WO | WO 03/042691 | 5/2003 |
| WO | WO 00/06024 | 2/2000 | WO | WO 03039369 A | 5/2003 |

| | | | | | | |
|---|---|---|---|---|---|---|
| WO | WO 03/045557 | 6/2003 | | WO | WO 2005/034720 | 4/2005 |
| WO | WO 03/046542 | 6/2003 | | WO | WO 2005/034721 | 4/2005 |
| WO | WO 03/049609 | 6/2003 | | WO | WO 2005/034741 | 4/2005 |
| WO | WO 03/050534 | 6/2003 | | WO | WO 2005/034778 | 4/2005 |
| WO | WO 03/066128 | 8/2003 | | WO | WO 2005/035017 | 4/2005 |
| WO | WO 03/070099 | 8/2003 | | WO | WO 2005/035018 | 4/2005 |
| WO | WO 03/071940 | 9/2003 | | WO | WO 2005/037095 | 4/2005 |
| WO | WO 03/082091 | 10/2003 | | WO | WO 2005/046477 | 5/2005 |
| WO | WO 03/088824 | 10/2003 | | WO | WO 2005/065399 | 7/2005 |
| WO | WO 03/088834 | 10/2003 | | WO | WO 2005/065414 | 7/2005 |
| WO | WO 03/088835 | 10/2003 | | WO | WO 2005/065415 | 7/2005 |
| WO | WO 03/088851 A1 | 10/2003 | | WO | WO 2005/065545 | 7/2005 |
| WO | WO 03/094752 | 11/2003 | | WO | WO 2005/072604 | 8/2005 |
| WO | WO 03/101297 | 12/2003 | | WO | WO2005/084546 A2 | 9/2005 |
| WO | WO 2004/008130 | 1/2004 | | WO | WO 2005/084557 | 9/2005 |
| WO | WO 2004/022133 | 3/2004 | | WO | WO 2005/104948 | 11/2005 |
| WO | WO 2004/026130 | 4/2004 | | WO | WO 2005/114185 | 12/2005 |
| WO | WO 2004/040285 A2 | 5/2004 | | WO | WO 2005/116622 | 12/2005 |
| WO | WO 2004/040287 A1 | 5/2004 | | WO | WO 2005/119234 | 12/2005 |
| WO | WO 2004/040948 | 5/2004 | | WO | WO 2005/120197 | 12/2005 |
| WO | WO 2004/041082 | 5/2004 | | WO | WO 2005/120199 | 12/2005 |
| WO | WO 2004/045375 | 6/2004 | | WO | WO 2005/120365 | 12/2005 |
| WO | WO 2004/054455 | 7/2004 | | WO | WO 2005/121759 | 12/2005 |
| WO | WO 2004/060174 | 7/2004 | | WO | WO 2006/001797 | 1/2006 |
| WO | WO 2004/060446 | 7/2004 | | WO | WO 2006/001973 | 1/2006 |
| WO | WO 2004/091693 | 10/2004 | | WO | WO 2006/011062 | 2/2006 |
| WO | WO 2004/098405 | 11/2004 | | WO | WO 2006/013045 | 2/2006 |
| WO | WO 2004/003147 | 12/2004 | | WO | WO 2006/015615 | 2/2006 |
| WO | WO 2004/107964 | 12/2004 | | WO | WO 2006/027702 A2 | 3/2006 |
| WO | WO 2004/107975 | 12/2004 | | WO | WO 2006/031920 | 3/2006 |
| WO | WO 2004/112602 | 12/2004 | | WO | WO 2006/032391 | 3/2006 |
| WO | WO 2004/112612 | 12/2004 | | WO | WO 2006/072004 | 7/2006 |
| WO | WO 2005/001418 | 1/2005 | | WO | WO 2006/105146 | 10/2006 |
| WO | WO 2005/006939 | 1/2005 | | WO | WO 2006/116441 | 11/2006 |
| WO | WO 2005/011774 | 2/2005 | | WO | WO 2007/025635 | 3/2007 |
| WO | WO 2005/013824 | 2/2005 | | WO | WO 2007/044834 | 4/2007 |
| WO | WO 2005/016125 | 2/2005 | | WO | WO 2007/054335 | 5/2007 |
| WO | WO 2005/018425 | 3/2005 | | WO | WO 2007/070719 | 6/2007 |
| WO | WO 2005/018430 | 3/2005 | | WO | WO 2007/084367 | 7/2007 |
| WO | WO 2005/018454 | 3/2005 | | WO | WO 2007/088905 A1 | 8/2007 |
| WO | WO 2005/018709 | 3/2005 | | WO | WO 2007/106470 | 9/2007 |
| WO | WO 2005/018710 | 3/2005 | | WO | WO 2007/119900 | 10/2007 |
| WO | WO 2005/018711 | 3/2005 | | WO | WO 2008/112268 | 9/2008 |
| WO | WO 2005/022143 | 3/2005 | | WO | WO 2008/112279 | 9/2008 |
| WO | WO 2005/023088 | 3/2005 | | | | |
| WO | WO 2005/033659 | 4/2005 | | | | |

* cited by examiner the needle or lancet to a depth deeper than necessary produces excessive pain and trauma to the skin tissue. In patients such as diabetics, who have to sample blood often, any excessive pain or tissue trauma is a disincentive to comply with the blood sampling routine.
APPARATUS AND METHOD FOR PENETRATION WITH SHAFT HAVING A SENSOR FOR SENSING PENETRATION DEPTH

CROSS-REFERENCE TO RELATED APPLICATION

This application is a continuation of U.S. Ser. No. 10/008,159 filed Nov. 6, 2001 now U.S. Pat. No. 7,780,631, which is a continuation of U.S. Ser. No. 09/050,853 filed Mar. 30, 1998 (now U.S. Pat. No. 6,391,005), both of which applications are fully incorporated herein by reference.

FIELD OF THE INVENTION

The present invention is related to techniques for penetration of an object with a shaft and more particularly to apparatuses and methods for determining the penetration depth of a hypodermic needle.

BACKGROUND OF THE INVENTION

When inserting a long structure into an object, such as a needle into the tissue of a patient, it is often necessary to know how deep the penetration is. Penetration past the required depth for a desired result wastes effort and causes undue discomfort to the patient. Often the information is needed in a short time because further penetration may cause unnecessary damage to the object and it is desirable to stop the penetration once a predetermined depth is reached. For example, the analysis and quantification of blood components is an important diagnostic tool for better understanding the physical condition of a patient and blood samples need to be obtained by inflicting a wound by a needle or lancet. Inserting the needle or lancet to a depth deeper than necessary produces excessive pain and trauma to the skin tissue. In patients such as diabetics, who have to sample blood often, any excessive pain or tissue trauma is a disincentive to comply with the blood sampling routine.

The skin is consisted of two layers—the epidermis and the dermis. The capillary structures connected to the arterial and venous vascular beds rise vertically and are located in the dermis layer. The neural sensors such as Meissner's corpuscles and free nerve endings are also located in the dermis. Layers of subcutaneous tissues lie below the dermis. The supply arterial and venous capillaries are located laterally in this tissue bed. There is also adipose tissue interleaved with afferent and efferent nerve fibers along with their associated sensors interwoven within the vascular bed. The thicknesses of these tissue layers differ from individual to individual. Currently, commercially available needle or lancet for puncturing skin have preset penetration depth based on experimental data from lancing, thus, there is no certainty that the optimal depth of penetration is reached every time such a needle or lancet is used. To avoid unsuccessful blood sampling due to inadequate depth, a patient often overpenetrates the skin, causing unnecessary pain.

What is needed is a needle or lancet for sampling blood that can be used for inserting to the optimal depth without over or under penetration. Similarly, there is a need in other penetration applications for inserting a long shaft into an object without over or under penetration.

SUMMARY OF THE INVENTION

In the present invention, the depth of penetration of an elongated structure into an object is determined by an impedance sensor that senses the impedance of the material penetrated by the elongated structure at the tip of the elongated structure.

In one aspect, the present invention provides an apparatus having a shaft for penetration into an object which has impedance that varies according to the depth under a surface of the object. The apparatus contains a shaft that includes a shaft body having a tip for penetration and two conductive ends near the tip. The two conductive ends are near the tip such that a change of impedance of the material of the object sensed between the conductive ends will provide information on whether the desired depth of penetration has been reached.

This invention is especially applicable in obtaining blood from a patient by puncturing the skin because a shaft of the present invention takes advantage of the electrical impedance differences between deeper layers of skin tissue relative to the more shallow upper layer. The impedance can be monitored by, for example, a metallic needle that pierces the layers of skin tissue. When the needle initially penetrates into the outer epidermis and dermis layers of the skin, an initial high impedance is seen. A decline in the impedance is observed as the needle approaches the adipose layer.

Using the apparatus, including the shaft of the present invention, optimal penetration into an object that has electrical impedance which varies with penetration depth can be achieved. In the case of obtaining blood from a patient by inserting a needle into the skin, this can minimize the trauma and pain of overpenetration, as well as avoid the frustration and pain of unsuccessful blood sampling because of inadequate penetration. Such reduction of discomfort and tissue damage can significantly improve the compliance of patients with a blood sampling routine, for example.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect, the present invention provides a technique for sensing the depth of penetration when inserting a shaft into a body. As used herein, the term "shaft" refers to an object with a generally elongated body with a tip for penetrating the body of interest. The body of the shaft, depending on the application, can be rigid or somewhat flexible. Preferably, the tip has a relative sharp point or beveled lancet to facilitate penetration. The point is adequate sharp such that the shaft can be pushed into the body without the need for passing along a preexisting hole. The body of the shaft can have a cross section that is round or non-round (e.g., having a rectangular cross section). As an example, a needle-sized shaft suitable for hypodermic insertion is described in the following embodiments. It is to be understood that other non-hypodermic shafts, including shafts for non-medical purposes, can be made and used according to the present invention.

Needles and Lancets

Figure 1:
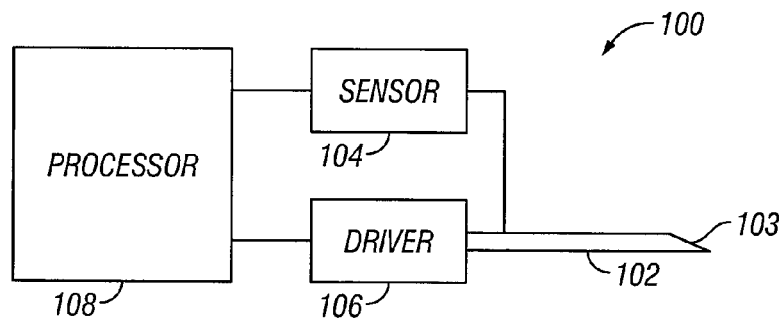
FIG. 1 shows an embodiment of an apparatus of the present invention.

FIG. 1 shows an embodiment of an apparatus for driving a shaft for penetrating skin according to the present invention. In FIG. 1, the apparatus 100 includes a shaft 102 (e.g., a needle or lancet) with conductive ends for sensing the impedance of tissue about the tip 103 of the shaft 102. An impedance sensor 104 (which includes electrical circuitry that senses impedance) electrically connected to the conductive ends senses the electrical impedance: Electrical devices and circuits that sense the electrical impedance between two points, e.g., in a material or in a circuit, are known in the art. An electrically controlled driver 106 drives the shaft 102 to penetrate the skin of the patient and tissue under it, which can be referred to as the "substrate" of penetration. The driver 106 is controlled by a processor 108, which stops the driver when the impedance sensor 104 senses an impedance change indicating the desired penetration has been achieved.

Figure 2A:
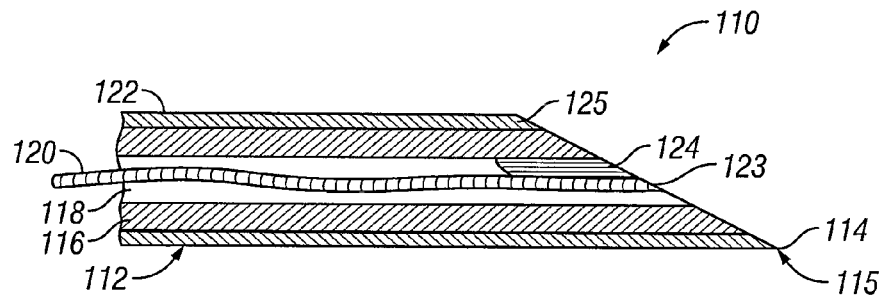
FIGS. 2A and 2B show an embodiment of a shaft of the present invention.
Figure 2B:
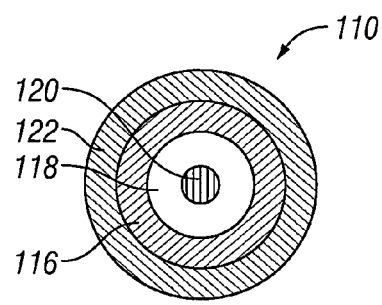

For illustration, FIG. 2A shows an embodiment of a portion of a hypodermic needle 110 that can be used in the present invention, e.g., as the shaft 102 in the apparatus 100. FIG. 2A is a sectional view along the axis of the hypodermic needle 110 and FIG. 2B shows a cross section of the hypodermic needle 110. The hypodermic needle 110 includes a stiff shaft body 112 having a sharp tip 114 at the distal end 115 for penetration into tissue. The shaft body 112 has a stiff, electrically non-conductive (e.g., polymeric, such as polyimide) tubing 116 with a central lumen 118 at the axis of the tubing 116. An electrically conductive (e.g., metallic tungsten) wire 120 located at the approximate axis of the tubing 116 extends from the sharp tip 114 proximally. The tungsten wire 120 has a distal conductive end 123 proximate to the distal end 115. As used herein, the term "distal" refers to the direction towards the object (e.g. the patient's skin) when the needle is about to penetrate the object and the term "proximal" refers to the direction opposite to that of "distal," therefore away from the object. An electrically conductive coating 122 (e.g., chrome/gold plated coating) is disposed on the outer surface of the nonconductive tubing 116 and has conductive end 125 at the tip 114. An adhesive 124 (see FIG. 2A), preferably electrically conductive, such as a silver epoxy, is used to attach the distal end of the electrically conductive wire 120 to the distal end 115 of the hypodermic needle 110.

Furthermore, if desired, a chamber or reservoir can be connected to the lumen 118 for collection of the fluid that may conduct through the lumen. This chamber or reservoir can be a nonconductive bag, a syringe, other tubings connected to the lumen, and the like.

Such a hypodermic needle can be made by, for example, electroplating a polyimide tubing to deposit the electrically conductive coating on the polyimide tubing and inserting, for example, a tungsten wire into the polyimide tubing and affixing an end of the wire to the distal end of the hypodermic needle with a silver epoxy. The distal end can be sharpened after all the conductive materials are in place. The proximal end of the electrically conductive wire 120 and the proximal end of the electrically conductive coating 122 can be connected to the impedance sensor 104 in the apparatus 100, or other similar equipment for sensing the penetration depth of the hypodermic needle 110. Other suitable materials for making the electrically conductive coating include, for example, silver, nickel, platinum, titanium, and tungsten. Materials suitable for making the electrically conductive wire include, for example, silver, nickel, platinum, titanium, gold, copper, aluminum, and tungsten.

Figure 3:
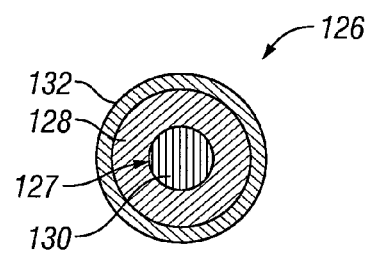
FIG. 3 shows another embodiment of a shaft of the present invention.

In another embodiment, as shown in FIG. 3, a solid needle assembly 126 can be made by filling the lumen 127 of a hollow nonconductive needle 128 with a conductive material 130 and coating on the non-conductive needle with a metallic coating 132. The resultant elongated structure can be modified to produce a sharp tip. Alternatively, a non-conductive material can be coated on a stiff metallic wire and then an outer coat of conductive metal can be coated on the non-conductive material to form a solid needle. Such a needle will have a structure similar to that shown in FIG. 3, which shows a cross section of the shaft.

To further stiffen a needle shaft for penetration, the needle having conductors leading to the distal end can be further coated with a material that provides additional rigidity. Many hard materials, such as metals or alloys are known in the art. An example of a material suitable for providing such additional rigidity is titanium nitride.

Figure 4:
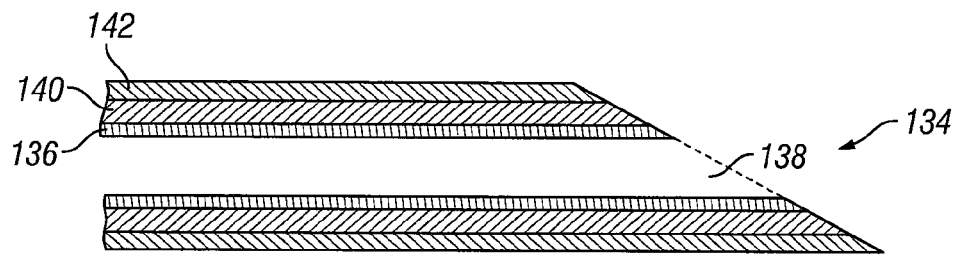
FIG. 4 shows yet another embodiment of a shaft of the present invention.

FIG. 4 shows another embodiment of a hypodermic needle of the present invention. In the hypodermic needle 134 shown in FIG. 4, an inner electrically conductive tubing 136 with a lumen 138 has a coating of a non-conductive material 140 electrically insulating the inner-WM-rig-136 from an electrically conductive coating 142 that is more remote from the axis. This hypodermic needle 134 can be made by coating, e.g., a steel needle with a non-conductive material and then sputtering a metallic coating on the electrically non-conductive material and further electroplating to form the outer electrically conductive coating 142.

Figure 5A:
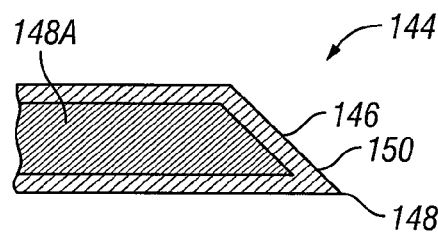
FIGS. 5A and 5B show a lancet of the present invention.
Figure 5B:
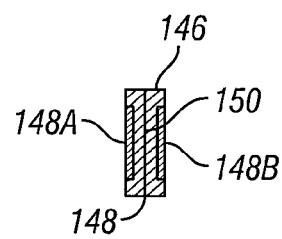

FIGS. 5A (a side view) and 5B (a front view) show yet another embodiment in which a shaft suitable for inserting into the skin of a patient has conductors for sensing impedance of the tissue surrounding the tip of the shaft. The shaft 144 has a rectangular cross section (see the front view of FIG. 5B) and has a central part 146 made of a stiff non-conductive material extending lengthwise along the shaft 144 sandwiched between two conductors 148A and 148B. The central part has a sharp tip 148 leading into a sharp edge 150 for cutting into a skin. Such a shaft can be used as a lancet for cutting a wound in the skin to yield blood.

Mechanisms for Driving the Shaft

A wide variety of drivers can be used to drive the shaft (including needles, lancets, blades) of the present invention. Such drivers can be electrically controlled such that when the desired depth has been achieved, the driver can be stopped, preferably, automatically. In this way, the depth of penetration can be optimized so that minimal penetration is used to achieve the desired result, such as drawing blood from a patient with the infliction of a minimal amount of pain and wound size. Examples of mechanisms that can be used for the driver include pneumatic, electromechanical, and piezoelectric mechanisms.

Figure 6A:
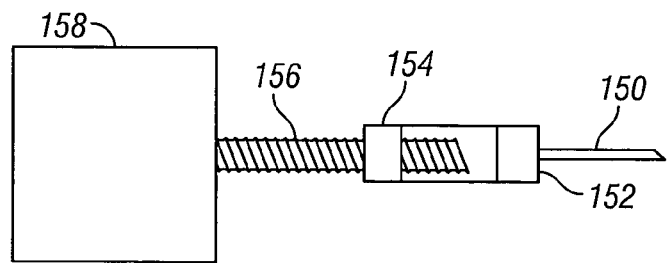
FIGS. 6A and 6B show apparatuses including an embodiment of a driver for driving a shaft according to the present invention.

FIG. 6A shows an apparatus with a driver for driving a shaft continually with a threaded mechanism. In the embodiment of FIG. 6A, the shaft 150 is affixed to a base 152 rigidly linked to a sleeve 154, which mates with a threaded rod 156. The threads of the sleeve 154 are so engaged with the threads of the threaded rod 156 such that the rotation of the threaded rod 156 will move the sleeve 154 along the threaded rod 156 axially. Therefore, a motor 158 that drives the rotation of threaded rod 156 in a direction (e.g. clockwise rotation) will drive the forward motion of the shaft 150 in the distal direction. Stopping the motor 158 will stop the forward advance of the shaft 150. Holding the motor 158 at a fixed position relative to the object to be penetrate and controlling the motor will control the depth of penetration of the shaft 150. Furthermore, the motor 158 can be driven to advance incrementally in an intermittent, stepwise fashion. If desired, the motor 158 can be operated to rotate in two directions to provide both forward and backward motion for advancing and withdrawing the shaft 150.

Figure 6B:
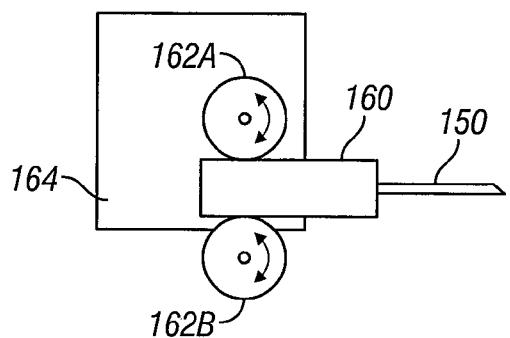

FIG. 6B illustrates another embodiment in which the shaft can be driven to advance continually. In this embodiment, a shaft 150 (e.g., a needle) is affixed to a base 160. The base 160 (and therefore the shaft 150) is driven to move in the forward, i.e., distal, direction by a rotor 162A that engages the base 160 on the side such that rotating the rotor 162A will move the base 160 and shaft 150 distally. The rotor 162A is driven by the a motor 164. Another rotor 162B engages the base 160 on a side opposite that of the rotor 162A for support. Either rotor 162A or rotor 162B can be an idler rotor. The rotors 162A and 162B can engage the base 160 by means of gears or by friction.

Figure 7A:
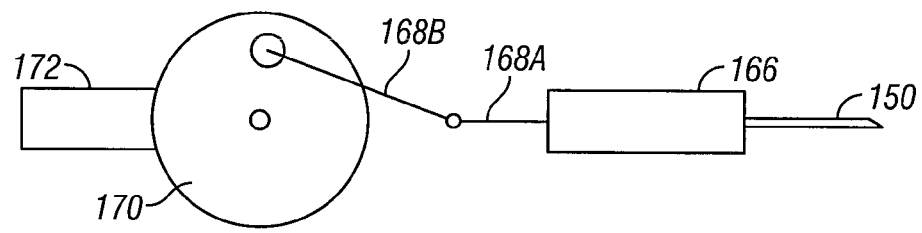
FIG. 7A shows an apparatus including an embodiment of a driver for driving a shaft.

FIG. 7A shows an embodiment of a shaft-penetration apparatus of the present invention with reciprocative action for inserting the shaft into a body. A shaft 150 is affixed to a link 166 actuated by linking arms 168A, 168B. The linking arms 168A and 168B are pivotably connected to each other. The linking arm 168B is pivotably connected off center to the rotor 170 which in turn is driven by motor 172. Thus, the rotation of the rotor 170 results in a back and forth reciprocative movement of the linking arms 168A, 168B, which is translated to the shaft 150. In addition, the whole system can be move steadily forward distally to advance the shaft 150 distally.

Figure 7B:
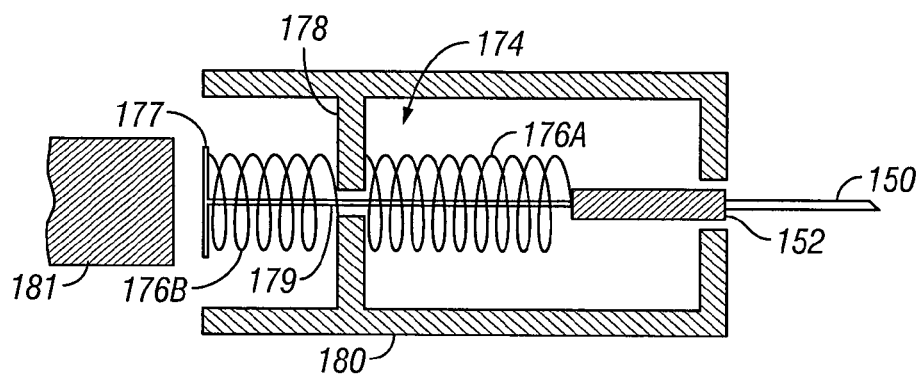
FIG. 7B shows an apparatus including a portion of an embodiment of a driver for driving a shaft.

FIG. 7B shows an embodiment of a spring mechanism 174 that can be used, e.g., as the link 166. The shaft 150, supported on a base 152 is held by the spring mechanism 174, which consists of a primary spring coil 176A and a secondary spring coil 176B. The primary spring coil 176A and secondary spring coil 176B are each held at one end by a ledge 178 of a housing 180, which houses the spring coils and part of the base 152. An end disk 177 is disposed at the proximal end of the spring coils 176A, 176B and affixed to the base 152 by a rigid rod 180 that extends through the axis of the spring coils 176A, 176B. A hammer 181 (shown in portion) can be used to impact the end disk 177, which drives the shaft 150 forward by means of rigid rod 180. After the impact, the springs 176A and 176B can move the shaft backward. It is noted that one of the springs 176A and 176B is optional and an alternative is to use only one of them.

Figure 8:
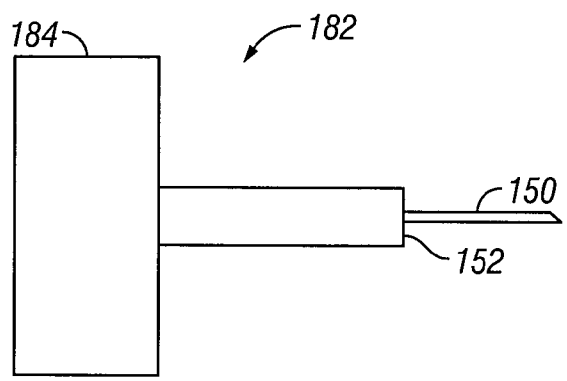
FIG. 8 shows an apparatus including a portion of a piezoelectric driver for driving a shaft.

FIG. 8 shows an example of a piezoelectric driver 182 for producing a reciprocative motion to drive a shaft for penetration. As in the aforementioned embodiments, a shaft 150 is affixed to a base 152, which is attached to a piezoelectric vibrator 184. When energized electrically, the piezoelectric vibrator 184 will vibrate to move the base 152 and the shaft 150 in a forward-backward motion. This whole vibrating driver system 182 can be advanced forward. Technique for making and using piezoelectric vibrators are known in the art and can be easily adopted for driving a shaft based on the present disclosure.

Figure 9:
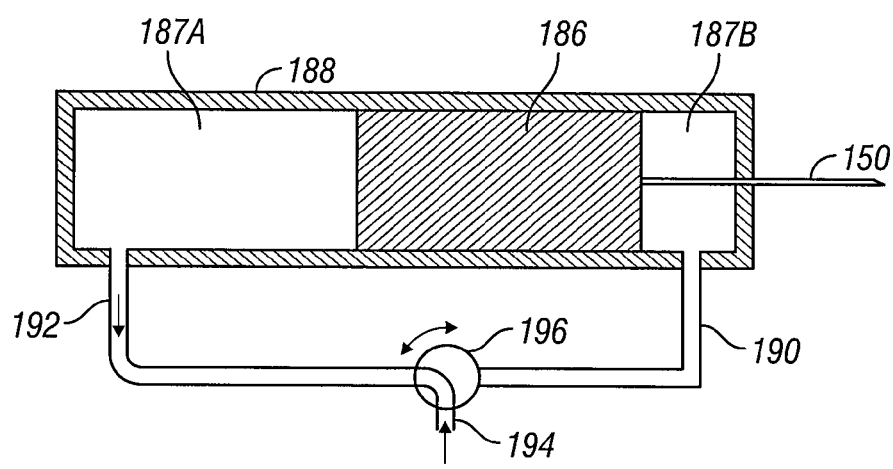
FIG. 9 shows an apparatus including a portion of a fluid-driven driver for driving a shaft.

FIG. 9 shows a fluid mechanism for driving a reciprocative motion for driving a shaft. Here, a shaft 150 is attached to a piston 186 that is allowed to slide inside a chamber (shown in the figure including he chamber 187A chamber 187B and the volume occupied by the piston 186) in a piston housing 188. A distal fluid conduit 190 distal to the piston 186 allows a fluid to enter the chamber 187B to drive the piston proximally, i.e., in a direction opposite to the distal direction. At the same time, preferably, a proximal fluid conduit inlet 192 proximal to the piston 186 can allow fluid to escape to facilitate the movement of the piston without building excessive pressure in the chamber 187A. Conversely, the proximal fluid conduit 192 can allow fluid to enter the chamber 187A to drive the piston distally while the distal fluid conduit 190 allows fluid to escape. A common fluid inlet conduit 194, connected to a multi-way valve 196 (e.g., three-way valve) can allow fluid to enter the proximal fluid conduit 192 or distal fluid conduit 190. Alternately admitting fluid into the chamber 187 proximal and distal to the piston while at the same time releasing fluid on the opposite side of the chamber will result in a reciprocative motion. To effect a progressive advance of the shaft 150 at the distal direction, over time, more fluid can enter the proximal conduit 192 than the distal fluid conduit 190. Optionally, one or both of the chambers 187A and 187B can be kept close to the environmental pressure so as to not put too much stress on the structure of the mechanism. Alternatively, the whole mechanism shown in FIG. 9 can be advanced while it is reciprocatively moving. A gas or a liquid can be used as the fluid for entering the chamber 187 to drive the progressive movement of the shaft 150.

The present invention can also find application in which the shaft advances in a sawing action. An example of such an apparatus has an elongated structure for conducting blood with an outer tube and an inner tube. The tubes associated with each other in concentric, close proximity with low friction between them so that one can slide on the other freely. The distal ends of the tubes each has a circular sharp cutting edge. The tubes are driven to move longitudinally reciprocatively such that alternately the sharp ring-shaped end of the outer tube is more distal than the end of the inner tube and the sharp ring-shaped end of the inner tube is more distal than the end of the outer tube. In this way, the elongated structure can penetrate' the tissue by a sawing action by the two tubes.

Figure 10:
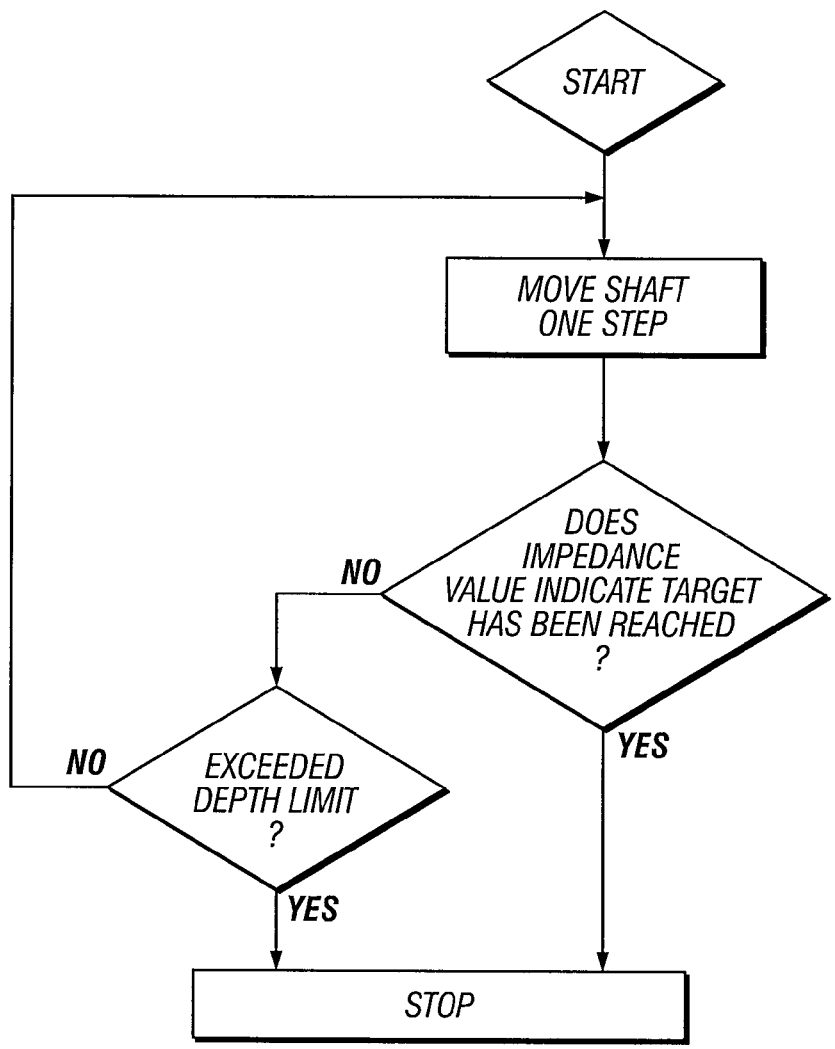
FIG. 10 shows a flow diagram for an algorithm for controlling the driver for driving a shaft according to the present invention.

The driving mechanism for driving the shaft (e.g., needle, lancet, and the like) of the present invention can be controlled by feedback electronics circuits that inhibit further shaft penetration once a proper depth of fluid material has been sensed. Typically, such a control system would be placed in the processor shown in FIG. 1. A control algorithm for such a control-system is illustrated by an exemplary flow diagram shown in FIG. 10. In this algorithm, once initiated, the driver will move the shaft one step at a time to advance an incremental distance until either the impedance measured indicate that the shaft has reach the target area (e.g. blood in capillary bed by a needle penetrating skin) or until the predetermined depth of penetration has been reached, at which point the driver will be stopped by the control circuitry. Whether the proper depth has been reached by the shaft can be determined by the magnitude of the change in impedance or the magnitude of the impedance itself. The selection of impedance values or jump values can be done by one skilled in the art. A processor can be provided external to the object that is being penetrated by the shaft for gathering and processing the impedance information to determine whether the desired depth has been achieved, as well as to control the movement of the shaft. Electrical devices and electrical circuits for processing information, controlling drivers, as well as those for sensing electrical impedance are known in the art. Such devices and circuits could include computers or microprocessors.

To use the apparatus of the present for the optimal benefit, preferably, the change in impedance with the depth of penetration is determined experimentally. After a few times of sampling, the apparatus can be adjusted to set the depth of insertion in relation to impedance changes to fit the particular preferences (e.g., penetration depth and sample volume) of that individual. Another way would be to obtain impedance data versus depth specifically for an individual patient and, after taking data from a plurality of blood samples, use the resultant data for setting the depth of penetration for future blood samples.

Although the preferred embodiment of the present invention has been described and illustrated in detail, it is to be understood that a person skilled in the art can make modifications within the scope of the invention. For example, it is understood that the present invention can be applied in a wide variety of medical or nonmedical areas, e.g., drilling in the ground for water, gas, petroleum, etc.

What is claimed is:

1. A tissue penetrating device for sampling body fluid from a patient and for use with a penetrating member, the device comprising:
    a driver coupled to provide force that moves said penetrating member along a path into the tissue;
    a controller coupled to the driver, the controller configured to control the driver and a motion of the penetrating member to reduce over-penetration by the penetrating member with reduced patient discomfort and
    wherein the driver is electrically controlled such that when a desired depth has been achieved, the driver is automatically stopped and a depth of penetration optimized so that minimal penetration is used to for drawing blood from a patient with an infliction of a minimal amount of pain and wound size.

2. The device of claim 1, further comprising:
    an electronic feedback loop circuit in electrical communication with a sensing device and the controller to inhibit penetrating member penetration once a penetration depth of the penetrating member has been sensed by the sensing device.

3. The device of claim 1, wherein the controller is configured to provide for the penetrating member to enter a tissue site through a skin surface at a velocity greater than an exit velocity from the tissue site.

4. The device of claim 1, wherein the controller provides control of the electronic driver such that when a desired depth of penetration at the tissue site by the penetrating has been achieved the electronic driver is stopped automatically.

5. The device of claim 1, wherein the electrical driver includes a motor.

6. The device of claim 1, wherein the controller includes a microprocessor.

7. The device of claim 6, wherein the controller has logic for directing the electrical driver to provide force to drive the penetrating member into tissue and to provide force to withdraw the penetrating member from tissue.

8. A tissue penetrating device for sampling body fluid from a patient and for use with a penetrating member, the device comprising:
    an electrical driver coupled to provide force that moves said penetrating member along a path into the tissue;
    a sensing device for use in controlling motion of the penetrating member to penetrate the skin of the patient to a desired depth of penetration that is sufficient to create a wound from which blood flows from the wound and into an interior of the tissue penetrating device for blood analysis, wherein at least a portion of the sensing device is coupled to move with the penetrating member as the penetrating member advances into the tissue;
    a controller electrically coupled to the electrical driver and sensing device, the controller having logic for directing the electrical driver to provide force to drive the penetrating member into tissue and to provide force to withdraw the penetrating member from tissue, the controller configured to receive a signal from the sensing device to control the electrical driver and a motion of the penetrating member to reduce over-penetration by the penetrating member with reduced patient discomfort and
    wherein the driver is electrically controlled such that when a desired depth has been achieved, the driver is automatically stopped and a depth of penetration optimized so that minimal penetration is used to for drawing blood from a patient with an infliction of a minimal amount of pain and wound size.

9. The device of claim 8, further comprising:
    an electronic feedback loop circuit in electrical communication with the sensing device and the controller to inhibit penetrating member penetration once a penetration depth of the penetrating member has been sensed by the sensing device.

10. The device of claim 9, wherein the controller is configured to provide for the penetrating member to enter a tissue site through a skin surface at a velocity greater than an exit velocity from the tissue site.

11. The device of claim 8, wherein the electrical driver in combination with the controller provides an electronic stop to stop travel of the penetrating member in the tissue site.

12. A tissue penetrating device for sampling blood from the skin of a patient, the device comprising:
    an electrical driver configured to provide drive force to a penetrating member, wherein said penetrating member is coupled to a sensing device;
    a controller electrically coupled to the electrical driver and configured to control a motion of the penetrating member to penetrate the skin of the patient to a desired depth of penetration that is sufficient to create a wound from which blood flows from the wound without flowing through the penetrating member and into an interior of the tissue penetrating device for blood analysis with reduced patient discomfort from the creation of the wound;
    an electronic feedback loop in electrical communication with the controller for inhibiting penetrating member penetration once a desired penetration depth of the penetrating member has been reached and control the electrical driver and a motion of the penetrating member to reduce over-penetration by the penetrating member with reduced patient discomfort sensed by the sensing device member; and
    wherein the electrical driver is used to stop the penetrating member in the tissue site and the driver is electrically controlled such that when a desired depth has been achieved, the driver is automatically stopped and a depth of penetration optimized so that minimal penetration is used to for drawing blood from a patient with an infliction of a minimal amount of pain and wound size.

13. The device of claim 12, wherein the electrical driver includes a motor.

14. The device of claim 12, wherein the controller includes a microprocessor.

15. A tissue penetrating device for sampling blood from a tissue site of a patient, comprising, an electrical driver including a sensing device, said electrical driver providing drive force, and configured to be coupled to and drive a penetrating member for penetrating a skin surface of a patient, wherein motion of the penetrating member results in motion of at least one component of the sensing device relative to the housing;

a controller coupled to the electrical driver and configured to control a motion of the penetrating member;

an electronic feedback loop circuit in electrical communication with the sensing device and the controller for inhibiting penetration of the penetrating member when a desired penetration depth of the penetrating member has been sensed by the sensing device member to penetrate the skin of the patient to a desired depth of penetration in the tissue site with reduced patient discomfort from the creation of the wound; and wherein using the electrical driver is used to stop the penetrating member in the tissue, the driver is electrically controlled such that when a desired depth has been achieved, the driver is automatically stopped and a depth of penetration optimized so that minimal penetration is used to for drawing blood from a patient with an infliction of a minimal amount of pain and wound size.

16. The device of claim 15, wherein the electrical driver includes a motor.

17. The device of claim 15, wherein the controller includes a microprocessor.

* * * * *